(12) United States Patent
Burton et al.

(10) Patent No.: US 11,272,709 B2
(45) Date of Patent: Mar. 15, 2022

(54) AMIDINE SUBSTITUTED BENZOYL DERIVATIVES USEFUL AS HERBICIDES

(71) Applicant: Syngenta Participations AG, Basel (CH)

(72) Inventors: Paul Matthew Burton, Bracknell (GB); Alexander Martin Richard Smith, Bracknell (GB); Katie Emery, Bracknell (GB)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/963,061

(22) PCT Filed: Jan. 16, 2019

(86) PCT No.: PCT/EP2019/051071
§ 371 (c)(1),
(2) Date: Jul. 17, 2020

(87) PCT Pub. No.: WO2019/141740
PCT Pub. Date: Jul. 25, 2019

(65) Prior Publication Data
US 2020/0345009 A1    Nov. 5, 2020

(30) Foreign Application Priority Data

Jan. 19, 2018 (GB) ..................... 1800894

(51) Int. Cl.
| | | |
|---|---|---|
| *A01N 43/713* | (2006.01) | |
| *A01N 37/52* | (2006.01) | |
| *A01N 43/82* | (2006.01) | |
| *C07C 251/16* | (2006.01) | |
| *C07C 251/24* | (2006.01) | |
| *C07D 257/06* | (2006.01) | |
| *C07D 271/113* | (2006.01) | |

(52) U.S. Cl.
CPC .......... *A01N 43/713* (2013.01); *A01N 37/52* (2013.01); *A01N 43/82* (2013.01); *C07C 251/16* (2013.01); *C07C 251/24* (2013.01); *C07D 257/06* (2013.01); *C07D 271/113* (2013.01)

(58) Field of Classification Search
None
See application file for complete search history.

(56) References Cited

FOREIGN PATENT DOCUMENTS

| WO | 0046184 A1 | 8/2000 |
|---|---|---|
| WO | 03074475 | 9/2003 |
| WO | 2008110278 A2 | 9/2008 |
| WO | 2013064459 A1 | 5/2013 |
| WO | 2017102275 A1 | 6/2017 |

OTHER PUBLICATIONS

International Search Report and Written Opinion for International Application No. PCT/EP2019/051071 dated Mar. 6, 2019.

*Primary Examiner* — Joseph R Kosack
(74) *Attorney, Agent, or Firm* — BakerHostetler; Toni-Junell Herbert

(57) ABSTRACT

The present invention related to compounds of Formula (I): or an agronomically acceptable salt thereof, wherein Q, X, Z, R² and R³ areas described herein. The inventions further relates to compositions comprising said compounds, to methods of controlling weeds using said compositions, and to the use of Compounds of Formula (I) as a herbicide.

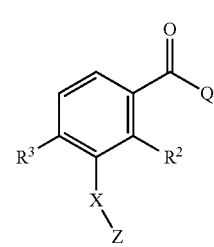

(I)

14 Claims, No Drawings

AMIDINE SUBSTITUTED BENZOYL DERIVATIVES USEFUL AS HERBICIDES

CROSS-REFERENCE TO RELATED APPLICATIONS

This application is a 371 National Stage application of International Application No. PCT/EP2019/051071 filed Jan. 16, 2019 which claims priority to GB 1800894.6, filed Jan. 19, 2018, the entire contents of which applications are hereby incorporated by reference.

The present invention relates to novel herbicidal compounds, to processes for their preparation, to herbicidal compositions which comprise the novel compounds, and to their use for controlling weeds, in particular in crops of useful plants, or for inhibiting plant growth.

N-(tetrazol-5-yl)- and N-(1,3,4-oxadiazol-2-yl) arylcarboxamides are disclosed in, for example, WO2012/028579 and WO2012/126932 respectively. The present invention relates to novel amidine substituted benzoyl compounds.

Thus, according to the present invention there is provided a compound of Formula (I):

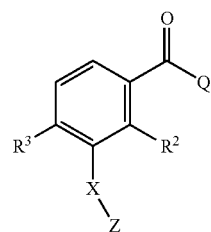

(I)

or an agronomically acceptable salt thereof,
wherein:—
$R^2$ is selected from the group consisting of halogen, $C_1$-$C_6$ alkyl, $C_3$-$C_6$-cycloalkyl, $C_1$-$C_6$ haloalkyl and —S(O)$_p$$C_1$-$C_6$ alkyl;
$R^3$ is selected from the group consisting of halogen, $C_1$-$C_6$ alkyl, $C_1$-$C_6$ haloalkyl and —S(O)$_p$$C_1$-$C_6$ alkyl;
Q is selected from the group consisting of $Q^1$, $Q^2$ and $Q^3$;

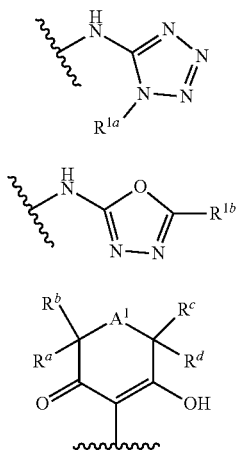

$R^{1a}$ is $C_1$-$C_4$alkyl- or $C_1$-$C_3$-alkoxy-$C_1$-$C_3$-alkyl-;
$R^{1b}$ is selected from the group consisting of hydrogen, $C_1$-$C_4$alkyl- and $C_1$-$C_3$-alkoxy-$C_1$-$C_3$-alkyl-;

$A^1$ is selected from the group consisting of O, C(O) and (CR$^e$R$^f$);
$R^a$, $R^b$, $R^c$, $R^d$, $R^e$ and $R^f$ are each independently selected from the group consisting of hydrogen and $C_1$-$C_4$alkyl wherein $R^a$ and $R^c$ may together form a $C_1$-$C_3$alkylene chain.
X is —(CH$_2$)$_n$— or —(CH$_2$)$_n$—O—(CH$_2$)$_n$—;
n is independently selected from 0, 1 and 2;
Z is $Z^1$ or $Z^2$

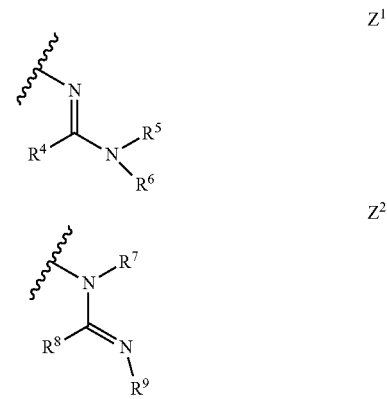

$R^4$ is selected from the group consisting of hydrogen, $C_1$-$C_6$ alkyl, $C_1$-$C_6$ haloalkyl and $C_3$-$C_6$ cycloalkyl;
$R^5$ is selected from the group consisting of hydrogen, $C_1$-$C_6$ alkyl and $C_1$-$C_6$ haloalkyl;
$R^6$ is selected from the group consisting of hydrogen, $C_1$-$C_6$ alkyl, $C_1$-$C_6$ haloalkyl, cyano and phenyl wherein the phenyl is optionally substituted by 1, 2 or 3 substituents selected from the group consisting of halogen, $C_1$-$C_6$ alkyl, $C_1$-$C_6$ haloalkyl and $C_1$-$C_6$ alkoxy; or
$R^5$ and $R^6$ together are —CH$_2$CH$_2$CH$_2$CH$_2$, —CH$_2$CH$_2$CH$_2$CH$_2$CH$_2$— or —CH$_2$CH$_2$OCH$_2$CH$_2$—; and
$R^7$ is selected from the group consisting of hydrogen and $C_1$-$C_6$ alkyl;
$R^8$ is selected from the group consisting of hydrogen, $C_1$-$C_6$ alkyl, $C_1$-$C_6$-haloalkyl and $C_3$-$C_6$-cycloalkyl;
$R^9$ is selected from the group consisting of hydrogen, cyano, $C_1$-$C_6$ alkyl and $C_1$-$C_6$alkoxy-; and
p=0, 1 or 2.

$C_1$-$C_6$alkyl and $C_1$-$C_4$alkyl groups include, for example, methyl (Me, CH$_3$), ethyl (Et, C$_2$H$_5$), n-propyl (n-Pr), isopropyl (i-Pr), n-butyl (n-Bu), isobutyl (i-Bu), sec-butyl and tert-butyl (t-Bu).

$C_3$-$C_6$cycloalkyl- includes cyclopropyl (c-propyl (c-Pr)), cyclobutyl (c-butyl (c-Bu)), cyclopentyl (c-pentyl) and cyclohexyl (c-hexyl).

Halogen (or halo) encompasses fluorine, chlorine, bromine or iodine. The same correspondingly applies to halogen in the context of other definitions, such as haloalkyl.

$C_1$-$C_6$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl-, heptafluoro-n-propyl and perfluoro-n-hexyl. $C_1$-$C_4$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl- and heptafluoro-n-propyl-.

$C_1$-$C_6$alkyl-S-(alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)-(alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$-(alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

In a preferred embodiment of the present invention, $R^2$ is selected from the group consisting of methyl, Cl, —$CF_3$ and —$SO_2$methyl.

In another preferred embodiment of the present invention, $R^3$ is selected from the group consisting of methyl, Cl, —$CF_3$ and —$SO_2$methyl.

In another preferred embodiment of the present invention, $R^{1a}$ and $R^{1b}$ are selected from the group consisting of methyl, ethyl and n-propyl.

In another embodiment of the present invention, Q is $Q^1$ and Z is $Z^1$. In this embodiment X can be —(CH$_2$)$_n$— and n is 0. In this embodiment the compound of Formula (I) is a compound of Formula (Ia):

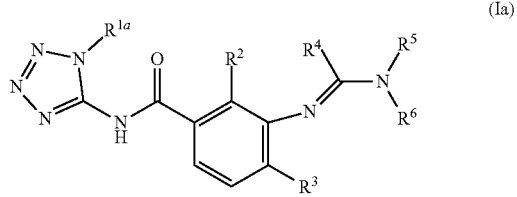

(Ia)

wherein $R^{1a}$, $R^2$, $R^1$, $R^4$, $R^5$ and $R^6$ are as defined with regard to a compound of Formula (I).

In another embodiment of the present invention, Q is $Q^2$ and Z is $Z^1$. In this embodiment X can preferably be —(CH$_2$)$_n$— and n is 0, or —CH$_2$O— (wherein the —CH$_2$ is attached to the phenyl ring and the O attaches to Z). Thus in another preferred embodiment of the present invention there is provided a compound of Formula (Ib)

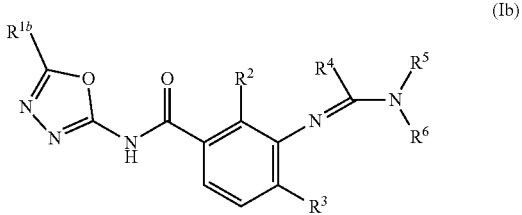

(Ib)

wherein $R^{1b}$, $R^2$, R, $R^4$, $R^5$ and $R^6$ are as defined with regard to a compound of Formula (I).

In another embodiment of the present invention, Q is $Q^3$ and Z is $Z^1$.

In another embodiment of the present invention, Q is $Q^1$ and Z is $Z^2$.

In another embodiment of the present invention, Q is $Q^2$ and Z is $Z^2$.

In another embodiment of the present invention, Q is $Q^3$ and Z is $Z^2$.

Compounds of Formula (I) (and certain intermediate compounds used to synthesise compound of Formula (I)) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

The present invention also includes all possible geometric and tautomeric forms of a compound of formula (I).

The present invention also includes agronomically acceptable salts that the compounds of Formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound of the present invention and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I).

Wetting agents, dispersing agents and emulsifying agents may be SFAs of the cationic, anionic, amphoteric or nonionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyru, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, +karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), I+4-hydroxy-1-methoxy-5-methyl-3-[4-(trifluoromethyl)-2-pyridyl]imidazolidin-2-one, I+4-hydroxy-1,5-dimethyl-3-[4-(trifluoromethyl)-2-pyridyl]imidazolidin-2-one, I+5-ethoxy-4-hydroxy-1-methyl-3-[4-(trifluoromethyl)-2-pyridyl]imidazolidin-2-one, I+4-hydroxy-1-methyl-3-[4-(trifluoromethyl)-2-pyridyl]imidazolidin-2-one, I+4-hydroxy-1,5-dimethyl-3-[1-methyl-5-(trifluoromethyl)pyrazol-3-yl]imidazolidin-2-one, I+(4R)1-(5-tert-butylisoxazol-3-yl)-4-ethoxy-5-hydroxy-3-methyl-imidazolidin-2-one, I+3-[2-(3,4-dimethoxyphenyl)-6-methyl-3-oxo-pyridazine-4-carbonyl]bicyclo[3.2.1]octane-2,4-dione, I+2-[2-(3,4-dimethoxyphenyl)-6-methyl-3-oxo-pyridazine-4-carbonyl]-5-methyl-cyclohexane-1,3-dione, I+2-[2-(3,4-dimethoxyphenyl)-6-methyl-3-oxo-pyridazine-4-carbonyl]cyclohexane-1,3-dione, 2-[2-(3,4-dimethoxyphenyl)-6-methyl-3-oxo-pyridazine-4-carbonyl]-5,5-dimethyl-cyclohexane-1,3-dione, I+6-[2-(3,4-dimethoxyphenyl)-6-methyl-3-oxo-pyridazine-4-carbonyl]-2,2,4,4-tetramethyl-cyclohexane-1,3,5-trione, I+2-[2-(3,4-dimethoxyphenyl)-6-methyl-3-oxo-pyridazine-4-carbonyl]-5-ethyl-cyclohexane-1,3-dione, I+2-[2-(3,4-dimethoxyphenyl)-6-methyl-3-oxo-pyridazine-4-carbonyl]-4,4,6,6-tetramethyl-cyclohexane-1,3-dione, I+2-[6-cyclopropyl-2-(3,4-dimethoxyphenyl)-3-oxo-pyridazine-4-carbonyl]-5-methyl-cyclohexane-1,3-dione, I+3-[6-cyclopropyl-2-(3,4-dimethoxyphenyl)-3-oxo-pyridazine-4-carbonyl]bicyclo[3.2.1]octane-2,4-dione, I+2-[6-cyclopropyl-2-(3,4-dimethoxyphenyl)-3-oxo-pyridazine-4-carbonyl]-5,5-dimethyl-cyclohexane-1,3-dione, I+6-[6-cyclopropyl-2-(3,4-dimethoxyphenyl)-3-oxo-pyridazine-4-carbonyl]-2,2,4,4-tetramethyl-cyclohexane-1,3,5-trione, I+2-[6-cyclopropyl-2-(3,4-dimethoxyphenyl)-3-oxo-pyridazine-4-carbonyl]cyclohexane-1,3-dione, I+4-[2-(3,4-dimethoxyphenyl)-6-methyl-3-oxo-pyridazine-4-carbonyl]-2,2,6,6-tetramethyl-tetrahydropyran-3,5-dione and 4-[6-cyclopropyl-2-(3,4-dimethoxyphenyl)-3-oxo-pyridazine-4-carbonyl]-2,2,6,6-tetramethyl-tetrahydropyran-3,5-dione. The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula I may also be in the form of esters or salts, as mentioned e.g. in The Pesticide Manual, $16^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of controlling weeds at a locus said method comprising application to the locus of a weed controlling amount of a composition comprising a compound of Formula (I). Moreover, the present invention further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow. Some crop plants may be inherently tolerant to herbicidal effects of compounds of Formula (I). However, in some instances tolerance may need to be engineered into the crop plant, for example by way of genetic engineering. Thus, it is possible that the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species. Several HPPD-tolerant soybean transgenic "events" are known, and include for example SYHT04R (WO2012/082542), SYHTOH2 (WO2012/082548) and FG72. Other polynucleotide sequences that can be used to provide plants which are tolerant to the compounds of the present invention are disclosed in, for example, WO2010/085705 and WO2011/068567. Crop plants in which the composition according to the invention can be used thus include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and Sorghum, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica*, Viola and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared according to the following schemes.

Compounds for formula (I) may be prepared from benzoic acids of formula (II).

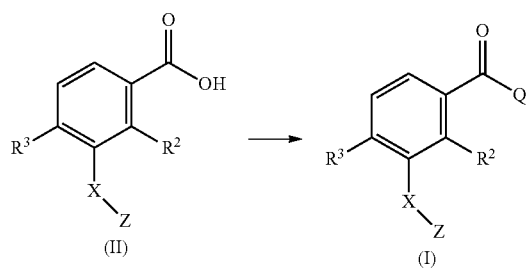

As shown in Scheme 1.1, where $Q=Q^1$, the benzoic acid of formula (II) is treated with an amine of formula (III) in the presence of a suitable amide coupling reagent in a suitable solvent. Examples of suitable amide coupling reagents are propylphosphonic anhydride (T3P) and 1,1'-carbonyldiimidazole (CDI). Examples of suitable solvents are dichloromethane and 1,4-dioxane.

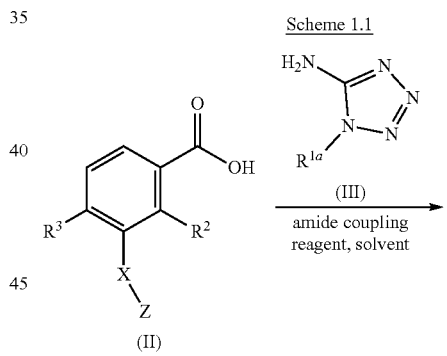

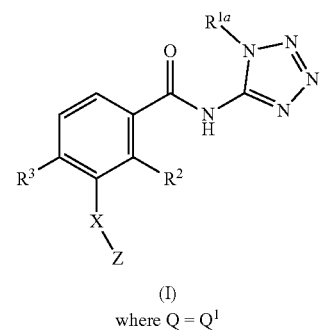

As shown in Scheme 1.2, where Q=Q², the benzoic acid of formula (II) is treated with an amine of formula (IV) in the presence of a suitable amide coupling reagent in a suitable solvent to give the compound of formula (I) where Q=Q². Examples of suitable amide coupling reagents are propylphosphonic anhydride (T3P) and 1,1'-carbonyldiimidazole (CDI). Examples of suitable solvents are dichloromethane and 1,4-dioxane.

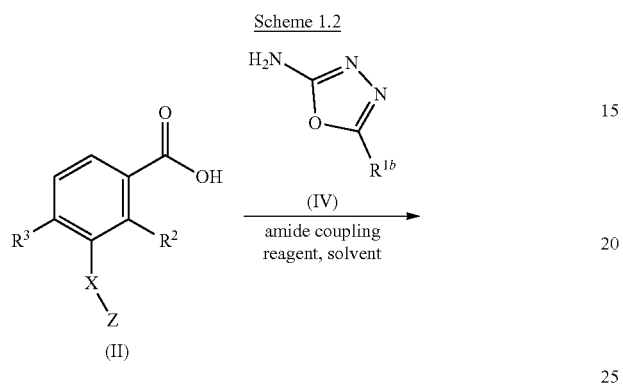

As shown in Scheme 1.3, where Q=Q³, the benzoic acid of formula (II) is treated with oxalyl chloride and catalytic DMF in dichloromethane. Once the chlorination is complete, triethylamine and a 1,3-dione of formula (V) is then added to the reaction mixture. After approximately 1 hour, catalytic acetone cyanohydrin is added to give the compound of formula (I) where Q=Q³.

Benzoic acids of formula (II) may be prepared from esters of formula (VI) as shown in Scheme 2, where "Alk" is defined as a $C_1$-$C_6$ alkyl, for example methyl or ethyl.

The ester of formula VI is treated with an alkoxide base, for example sodium hydroxide or lithium hydroxide and a suitable solvent. Two examples of a suitable solvent are: a 2:1 mixture of ethanol: water or a 2:1 mixture of tetrahydrofuran: water. Esters of formula (VI) may be prepared from a variety of means depending on the nature of Z. Where Z=$Z^1$, esters of formula (VI) may be prepared from anilines of formula (VII) and Vilsmeier salts of formula (VIII) as shown in Scheme 3:

Scheme 3

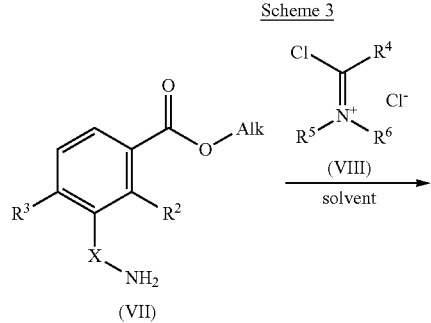

Some Vilsmeier salts are available commercially, such as (chloromethylene)dimethyliminium chloride. Following Scheme 3, the amine of formula (VII) is treated with the Vilsmeier salt of formula (VIII) in a suitable solvent, for example tetrahydrofuran.

Where Z=$Z^2$, compounds of formula (VI) may be prepared from thioamides of formula (IX) as shown in Scheme 4.

Scheme 4

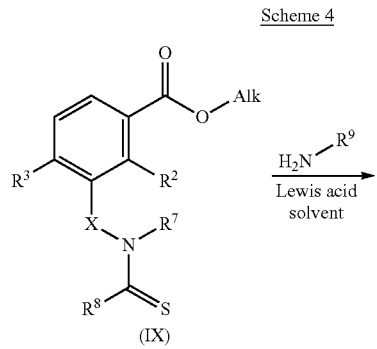

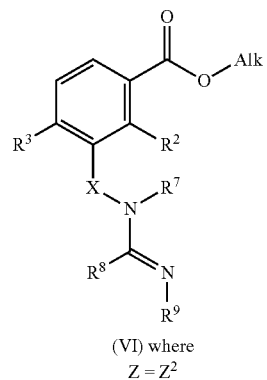

The thioamide of formula (IX) is treated with the appropriate amine $H_2N$—$R^6$ in the presence of a suitable Lewis acid and a suitable solvent. An example of a suitable Lewis acid is silver tetrafluoroborate. An example of a suitable solvent is tetrahydrofuran. Thioamides of formula (IX) may be prepared from amines of formula (X) as shown in Scheme 5, where "Alk" is a $C_1$ to $C_6$ alkyl such as methyl or ethyl.

Scheme 5

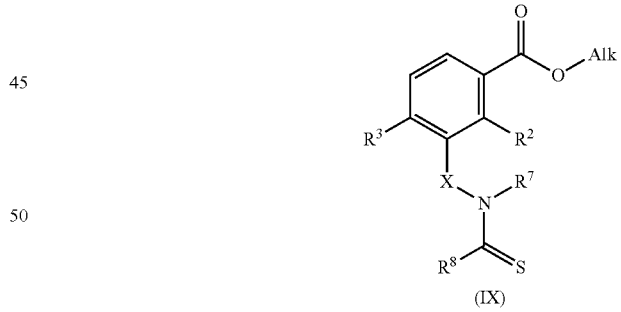

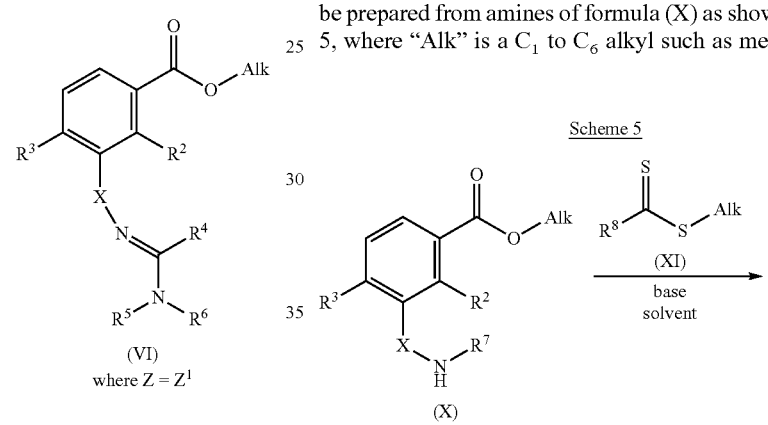

As shown in Scheme 5, the amine of formula (X) is treated with the appropriate dithioester of formula (XI) and a base in a suitable solvent. An example of a suitable base is triethylamine. An example of a suitable solvent is tetrahydrofuran. Amines of formula (X) may be prepared by alkylation of amines of formula (VII). Such methods of alkylation, for example reductive amination, should be familiar to the skilled person. Alternatively, amines of formula (X) may be prepared by amination of halides of formula (XII) as shown in Scheme 6, where "Hal" is a halogen atom such as chlorine or bromine.

Scheme 6

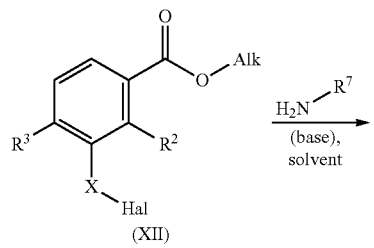

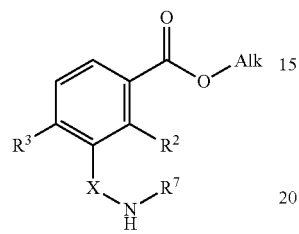

The halide of formula (XII) is treated with the appropriate amine H₂N—R⁷ in an appropriate solvent, for example tetrahydrofuran. A base may be used in this reaction. Alkyl halides of formula (XII) may be prepared by various methods. One example of their preparation, where X=—CH₂— is the bromination of methyl substituted benzene derivatives of formula (XIII).

Scheme 7

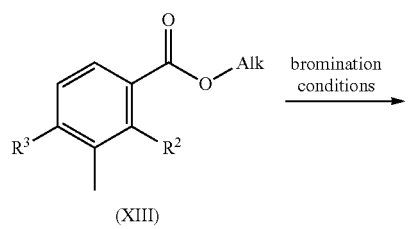

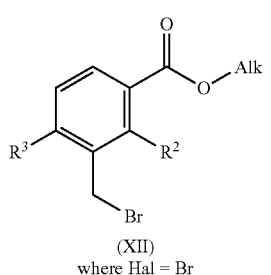

In this example, suitable bromination conditions are N-bromosuccinimide in the presence of a catalytic quantity of benzoylperoxide or azobisisobutyronitrile using CCl₄ or 1,2-dichloroethane as solvent. The synthesis of many examples of Compound of formula (XIII) are reported. Examples include ethyl 2-chloro-3-methyl-4-trifluoromethylbenzoate and ethyl 2-chloro-3-methyl-4-methylsulfonyl-benzoate. The synthesis of compound formula (VII) may derive from carboxylic acids of formula (XIV) by an esterification reaction as shown in Scheme 8.

Scheme 8

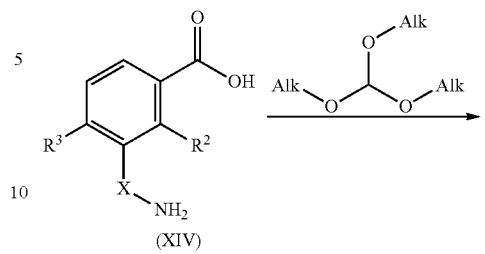

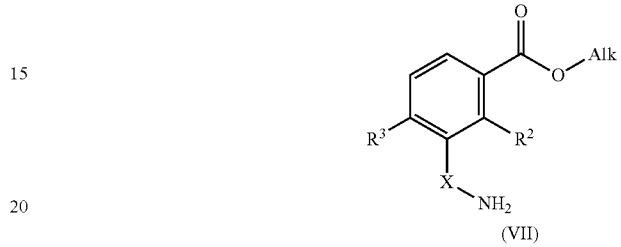

Compounds of formula (XIV) are heated in the appropriate orthoester to give compounds of formula (VII). For example, where Alk=ethyl, triethylorthoformate is used. The orthoester can be used as both reagent and solvent if it is a liquid. Compounds of formula (XIV) may be known in the literature or may be readily prepared from available starting materials. An example of a compound of formula (XIV) is 3-amino-2-methyl-4-(methylsulfonyl)benzoic acid.

The following non-limiting examples provide specific synthesis methods for representative compounds of the present invention, as referred to the Tables provided herein.

PREPARATIVE EXAMPLE 1: COMPOUND 1.025

Oxalyl dichloride (1.20 g, 9.4 mmol) was added dropwise to a solution of DMF (0.34 g, 4.7 mmol) in DCM (25 mL) at 0° C. (vigorous effervescence then a white suspension formed). The reaction mixture was allowed to stir for 30 min at room temperature and was then concentrated to dryness giving an off-white solid. This was suspended in dichloromethane (25 mL) and then ethyl 3-amino-2-methyl-4-methylsulfonyl-benzoate (600 mg, 2.33 mmol) was added as a solution in DCM (2 mL). Within a few seconds a yellow solution formed, which was stirred for 10 min. The reaction mixture was added dropwise to stirring sat. NaHCO₃ solution in an ice bath and stirred for 10 mins (care: effervescence). The organic layer was separated, extracted, with CHCl3:IPA (7:3 ratio, 2×10 mL) then dried and concentrated in vacuo. The material was loaded onto celite and purified by flash chromatography: Column: 40 g silica. Solvent A: Dichloromethane. Solvent B: Methanol. Gradient: 0-5% B in A over 15 min. Began to elute at 2% B in A. The fractions containing the product were combined and concentrated in vacuo and dried to give ethyl 3-[(E)-dimethylaminomethyleneamino]-2-methyl-4-methylsulfonyl-benzoate (665 mg, 2.13 mmol) as a yellow oil. 1H NMR (400 MHz, chloroform) δ=7.88 (d, J=8.3 Hz, 1H), 7.47 (d, J=8.3 Hz, 1H), 7.21 (s, 1H), 4.38 (q, J=7.1 Hz, 2H), 3.20 (s, 3H), 3.06 (br d, J=14.8 Hz, 6H), 2.33 (s, 3H), 1.40 (t, J=7.2 Hz, 3H).

To ethyl 3-[(E)-dimethylaminomethyleneamino]-2-methyl-4-methylsulfonyl-benzoate (660 mg, 2.11 mmol) in ethanol (12 mL) and water (3.4 mL) was added lithium hydroxide monohydrate (222 mg, 5.28 mmol). After 2 h, the mixture was concentrated in vacuo to remove ethanol. The residue was taken up in water and the aqueous solution was adjusted to pH 10 by addition of excess ammonia solution (38% in water). This solution was purified directly by liquid injection to reversed phase flash chromatography using a C-18 aq 50 g column. Solvent A: Water+0.1% ammonia. Solvent B: acetonitrile+0.1% ammonia. Gradient: 0% for 3 column volumes, then 0-50% B in A over 10 column volumes. Eluted at 0% B in A. The fractions containing product were combined and concentrated in vacuo, then the material was dissolved in water and freeze-dried overnight to give 3-[(E)-dimethylaminomethyleneamino]-2-methyl-4-methylsulfonyl-benzoic acid (496 mg, 1.75 mmol as a white solid). 1H NMR (400 MHz, DMSO-d6) δ=7.49 (d, J=8.1 Hz, 1H), 7.30 (s, 1H), 6.94 (d, J=8.1 Hz, 1H), 3.16 (s, 3H), 2.97 (s, 6H), 2.15-2.04 (m, 3H).

To a flask containing 3-[(E)-dimethylaminomethyleneamino]-2-methyl-4-methylsulfonyl-benzoic acid (245 mg, 0.862 mmol) was added anhydrous 1,4-dioxane (5 mL) and N,N'-carbonyldiimidazole (210 mg, 1.29 mmol). The mixture was stirred at 100° C. for 16 h then cooled to RT. 1-methyltetrazol-5-amine (128 mg, 1.29 mmol) and DBU (0.132 mL, 0.862 mmol) was added and the reaction mixture was stirred at 100° C. for 3 days. A further portion of 1-methyltetrazol-5-amine (128 mg, 1.29 mmol) and DBU (0.132 mL, 0.862 mmol) were then added and the reaction mixture was stirred at 100° C. for 2 h. The reaction was allowed to cool and then concentrated in vacuo. Water (10 mL) was added to the residue and DCM (10 mL). The mixture was separated and the aqueous phase was extracted with CHCl$_3$:IPA (7:3, 2×10 mL). The organic phases were combined, dried over MGSO$_4$, filtered and concentrated in vacuo. The material was loaded onto celite and purified by flash chromatography (0 to 10% MeOH/DCM) to give 3-[(E)-dimethylaminomethyleneamino]-2-methyl-4-methylsulfonyl-N-(1-methyltetrazol-5-yl)benzamide (136 mg, 0.372 mmol) as a white solid. 1H NMR (400 MHz, DMSO-d6) δ=7.71 (d, J=8.2 Hz, 1H), 7.39 (s, 1H), 7.30 (d, J=8.2 Hz, 1H), 3.88 (s, 3H), 3.24 (s, 3H), 3.00 (s, 6H), 2.18 (s, 3H).

PREPARATIVE EXAMPLE 2: COMPOUND 1.130

Added 2-[3-fluoro-4-(trifluoromethyl)phenyl]-4,4-dimethyl-5H-oxazole (14 g, 51 mmol) in 120 mL of dry THF to 500 mL 4-necked RBF equipped with a thermometer. Cooled the reaction mass to −74° C. and then added n-butyl lithium as a 2.0 M solution in hexane (36 mL, 71 mmol) drop-wise. Stirred the reaction mass at about −74° C. for another 1.5 h. To this solution then added the solution of hexachloroethane (8.8 mL, 77 mmol) in 40.3 mL of dry THF at −70° C. The mixture was stirred at about −70° C. for 30 min and then allowed to stand for 16 h, during which time TLC shows no starting material. The mixture was poured into ice-cold solution of 6N aq. HCl (40.30 mL) and extracted with EtOAc (750 ml×3). Combined organic phases then washed with brine, dried over Na$_2$SO$_4$, filtered and concentrated. The crude product was then purified by silica gel column chromatography and desired product was eluted with 4.0% EtOAc in Hexane to give 2-[2-chloro-3-fluoro-4-(trifluoromethyl)phenyl]-4,4-dimethyl-5H-oxazole (25 g, 28 mmol).

To the solution of tBuOK (15.4 g) in N,N-dimethylacetamide (96 mL) in a RBF was added formamide (14.5 mL) dropwise and stirred. After 15 min, a solution of 2-[2-chloro-3-fluoro-4-(trifluoromethyl)phenyl]-4,4-dimethyl-5H-oxazole (16 g) in N,N-dimethylacetamide (38 mL) was added. The mixture was then warmed to 120° C. for 2 h. The reaction mass was then cooled to room temperature and then poured into ice water (160 mL) and extracted with 30% solution of EtOAc in MTBE (160 ml×4). The combined organic layers were washed with brine, dried over Na$_2$SO$_4$, filtered and concentrated under high vacuum. Finally, the crude product was triturated with 5% solution of Et2O in Hexane to afford desired product N-[2-chloro-3-(4,4-dimethyl-5H-oxazol-2-yl)-6-(trifluoromethyl)phenyl]formamide (16.8 g) as off white solid.

N-[2-chloro-3-(4,4-dimethyl-5H-oxazol-2-yl)-6-(trifluoromethyl)phenyl]formamide (12 g, 37 mmol)) was taken in 52.2 mL of concentrated hydrochloric acid in an rbf, and the mixture was heated under reflux. After 4 h, the mixture was cooled on ice bath and resulting solid was filtered off and the residue was washed with cold water and then dried under high vacuum to give 3-amino-2-chloro-4-(trifluoromethyl) benzoic acid (9.0 g) as a solid. 1H NMR (d6-DMSO): 7.44 (1H, d), 6.92 (1H, d), 5.90 (2H, brs).

To the solution of 3-amino-2-chloro-4-(trifluoromethyl) benzoic acid (16 g, 58 mmol) in 78 mL DMF in an RBF was added 8.36 potassium carbonate and stirred at RT for 15 min. To that was then added 23.4 mL iodoethane and stirred at RT for 2 h. TLC & HPLC checked and reaction was completed. Reaction mixture was diluted with 750 mL cold water and extracted with TBME (250 mL×2). The combined TBME layers were washed with aq. Na2S2O3 solution, then with rine, dried over Na$_2$SO$_4$, filtered and concentrated to give ethyl 3-amino-2-chloro-4-(trifluoromethyl)benzoate (8 g, 27 mmol) as a black liquid.

Oxalyl dichloride (0.49 g, 0.34 mL, 3.8 mmol) was added dropwise to a colourless solution of N-methyl-N-(2,2,2-trifluoroethyl)formamide (268 mg, 1.9 mmol) in dichloromethane (12 mL). The reaction mixture was allowed to stir for 30 min (a yellow solution formed) and was then concentrated to dryness giving an orange oil. This was dissolved in dichloromethane (5 mL) and then ethyl 3-amino-2-chloro-4-(trifluoromethyl)benzoate (250 mg, 0.934 mmol) was added as a solution in DCM (1 ml). A yellow suspension formed. The reaction mixture was stirred for 5 min and LCMS analysis showed it to be complete. The reaction mixture was added dropwise to stirring sat. NaHCO$_3$ solution (10 mL) in an ice bath and stirred for 5 mins (care: effervescence). The organic layer was separated, and the aqueous layer was extracted a second time with dichloromethane (10 mL). LCMS showed the product in the aqueous layer. Extraction with CHCl3:IPA (7:3, 10 mL) successfully extracted the product out of the aqueous layer. The material was purified by flash chromatography (0 to 100% EtOAc/isohexane) to give ethyl 2-chloro-3-[(E)-[methyl(2,2,2-trifluoroethyl)amino]methyleneamino]-4-(trifluoromethyl)benzoate (330 mg, 0.845 mmol) as a colourless oil. NMR shows two rotamers. 1H NMR (400 MHz, chloroform) δ=7.53 (br d, J=8.1 Hz, 2H), 7.45-7.30 (m, 4H), 4.41 (q, J=7.2 Hz, 4H), 4.20 (q, J=8.9 Hz, 2H), 3.77 (q, J=8.4 Hz, 2H), 3.24-3.18 (m, 1H), 3.18-3.11 (m, 1H), 3.18 (br d, J=16.1 Hz, 4H), 1.40 (t, J=7.2 Hz, 6H).

To a stirred solution of ethyl 2-chloro-3-[(E)-[methyl(2,2,2-trifluoroethyl)amino]methyleneamino]-4-(trifluoromethyl)benzoate (320 mg, 0.819 mmol) in ethanol (5 mL) and water (1.5 mL) was added lithium hydroxide monohydrate (86 mg, 2.05 mmol) and the reaction mixture was stirred at room temperature for 30 min. The reaction mixture was concentrated in vacuo to remove EtOH. The mixture was diluted with DCM (10 mL) and then washed with 10% w/v citric acid in water (10 mL). The aqueous phase was extracted further with CHCl$_3$:IPA (7:3 ratio, 10 mL). LCMS shows only trace amount of product present in the aqueous phase. The organic layer was dried over $MgSO_4$, filtered and concentrated in vacuo to give 2-chloro-3-[(E)-[methyl(2,2,2-trifluoroethyl)amino]methyleneamino]-4-(trifluoromethyl)benzoic acid (250 mg, 0.689 mmol) as a yellow oil. 1H NMR (400 MHz, chloroform) δ=7.56 (d, J=4.2 Hz, 4H), 7.38 (br d, J=5.5 Hz, 2H), 4.21 (q, J=8.9 Hz, 2H), 3.85-3.75 (m, 2H), 3.19 (m, 6H).

To a flask containing 2-chloro-3-[(E)-[methyl(2,2,2-trifluoroethyl)amino]methyleneamino]-4-(trifluoromethyl)benzoic acid (125 mg, 0.345 mmol) was added anhydrous 1,4-DIOXANE (3 mL) and CDI (84 mg, 0.52 mmol). The mixture was stirred at 100° C. for 45 min, then cooled to RT.

To the reaction mixture was added 1-methyltetrazol-5-amine (51 mg, 0.52 mmol) and DBU (52 µL, 0.34 mmol). The reaction mixture was heated at 100° C. for 16 h. The reaction mixture was concentrated in vacuo. The crude material was diluted with $CH_2Cl_2$ (10 mL) and washed with aqueous sodium bicarbonate (10 mL). The aqueous phase was further extracted with $CHCl_3$:IPA (10 mL, 7:3). The organic phases were combined and dried over $MgSO_4$, filtered and concentrated in vacuo. The material was loaded onto celite and purified by flash chromatography (0 to 10% MeOH in $CH_2Cl_2$). The fractions containing the product were combined and concentrated in vacuo to give 2-chloro-N-(1-methyltetrazol-5-yl)-3-[(E)-[methyl(2,2,2-trifluoroethyl)amino]methylene amino]-4-(trifluoromethyl)benzamide (66 mg, 0.15 mmol) as a glassy solid. 1H NMR (400 MHz, chloroform) δ=11.21 (br s, 1H), 7.65-7.56 (m, 2H), 7.36 (br d, J=7.9 Hz, 1H), 4.21 (q, J=9.0 Hz, 0.9H), 4.12 (s, 3H), 3.84 (q, J=8.4 Hz, 1.1H), 3.21 (s, 3H) (note: rotamers present in NMR).

PREPARATIVE EXAMPLE 3: COMPOUND 1.132

Oxalyl dichloride (0.49 g, 0.34 mL, 3.8 mmol) was added dropwise to a colourless solution of pyrrolidine-1-carbaldehyde (0.18 mL, 1.9 mmol) in dichloromethane (4 mL). The reaction mixture was allowed to stir for 30 min (a yellow solution formed) and was then concentrated to dryness giving an orange solid. This was dissolved in dichloromethane (5 mL) and then ethyl 3-amino-2-chloro-4-(trifluoromethyl)benzoate (250 mg, 0.934 mmol) was added as a solution in dichloromethane (1 ml). A yellow suspension formed. The reaction mixture was stirred for 10 min and LCMS analysis showed it to be complete. The reaction mixture was added dropwise to stirring saturated $NaHCO_3$ solution (10 mL) in an ice bath and stirred for 5 mins. The organic layer was separated, and the aqueous layer was extracted a second time with dichloromethane (10 mL), then with $CHCl_3$:IPA (7:3, 10 mL). The reaction mixture was dried over $MgSO_4$, filtered and concentrated in vacuo. The material was purified by flash chromatography (0 to 20% EtOAc/isohexane) to give ethyl 2-chloro-3-[(E)-pyrrolidin-1-ylmethyleneamino]-4-(trifluoromethyl)benzoate (296 mg, 0.849 mmol) as a colourless oil. $^1$H NMR (400 MHz, chloroform) δ=7.50 (d, J=8.3 Hz, 2H), 7.29 (dd, J=0.6, 8.1 Hz, 1H), 4.41 (q, J=7.2 Hz, 2H), 3.63-3.45 (m, 4H), 1.99 (br dd, J=5.9, 14.1 Hz, 4H), 1.40 (t, J=7.2 Hz, 3H)

To a stirred solution ethyl 2-chloro-3-[(E)-pyrrolidin-1-ylmethyleneamino]-4-(trifluoromethyl)benzoate (296 mg, 0.849 mmol) in ethanol (4.8 mL) and water (1.4 mL) was added lithium hydroxide monohydrate (89 mg, 2.12 mmol) and the reaction mixture was stirred at room temperature for 2 h. The reaction mixture was concentrated in vacuo to remove ethanol. The mixture was diluted with water (2 mL), and ammonia solution (38% in water) was added dropwise until the aqueous solution was pH 10. The material was purified by reverse phase chromatography (0 to 12% acetonitrile+0.1% $NH_3$/water+0.1% $NH_3$). The fractions containing the product were combined and concentrated in vacuo to give 2-chloro-3-[(E)-pyrrolidin-1-ylmethyleneamino]-4-(trifluoromethyl)benzoic acid (242 mg, 0.755 mmol) as colourless crystals. $^1$H NMR (400 MHz, DMSO-$d_6$) δ=7.69 (s, 1H), 7.47 (d, J=8.2 Hz, 1H), 7.06 (d, J=7.9 Hz, 1H), 3.57-3.29 (m, 4H), 2.00-1.78 (m, 4H).

To a flask containing 2-chloro-3-[(E)-pyrrolidin-1-ylmethyleneamino]-4-(trifluoromethyl)benzoic acid (110 mg, 0.343 mmol) was added anhydrous 1,4-dioxane (3 mL) and CDI (83 mg, 1.5 equiv., 0.515 mmol). The mixture was stirred at 100° C. for 1 h, then cooled to room temperature. To the reaction mixture was added a second batch of CDI (83 mg, 1.5 equiv., 0.515 mmol). The reaction mixture was stirred at 100° C. for 1 h.

To the reaction mixture, DBU (52 mL, 1 equiv., 0.343 mmol) and 1-methyltetrazol-5-amine (51 mg, 1.5 equiv., 0.515 mmol) were added and the reaction mixture was stirred at 100° C. for 18 h. The reaction mixture was concentrated in vacuo. The crude material was diluted with $CH_2Cl_2$ (10 mL) and washed with aqueous sodium bicarbonate (10 mL). The aqueous phase was further extracted with $CHCl_3$:IPA (10 mL, 7:3). The organic phases were combined and dried over $MgSO_4$, filtered and concentrated in vacuo. The material was loaded onto celite and purified by flash chromatography (0 to 5% MeOH in $CH_2Cl_2$). The fractions containing the product were combined and concentrated in vacuo to give 2-chloro-N-(1-methyltetrazol-5-yl)-3-[(E)-pyrrolidin-1-ylmethyleneamino]-4-(trifluoromethyl)benzamide (47 mg, 0.12 mmol) as a white solid. $^1$H NMR (400 MHz, chloroform) δ=10.46 (br s, 1H), 7.58 (d, J=8.2 Hz, 1H), 7.49 (s, 1H), 7.30 (d, J=7.8 Hz, 1H), 4.09 (s, 3H), 3.63 (br s, 2H), 3.53 (br t, J=6.4 Hz, 2H), 2.11-1.94 (m, 4H)

PREPARATIVE EXAMPLE 4: COMPOUND 4.033

Starting Material from Preparative Example 7

To a solution of ethyl 2-chloro-3-[[ethanethioyl(methyl)amino]methyl]-4-methylsulfonyl-benzoate (100 mg, 0.275 mmol) in acetonitrile (5 mL) was added triethylamine (0.39 mL, 2.7 mmol), cyanamide (58 mg, 1.4 mmol) and silver tetrafluoroborate (270 mg, 1.37 mmol). The reaction mixture was stirred for 16 h overnight at RT. The solution was filtered and then concentrated in vacuo. The residue was dissolved in EtOAc (20 mL) and washed with postassium carbonate solution (20 mL), brine (20 mL), dried over magnesium sulfate and concentrated in vacuo. The product was purified by flash column chromatography (0-100% EtOAc/isohexane) to give ethyl 2-chloro-3-[[[N-cyano-C-methyl-carbonimidoyl]-methyl-amino]methyl]-4-methyl-sulfonyl-benzoate (77 mg, 0.21 mmol). NMR analysis showed the desired product exists as a mixture of isomers (~1:7). $^1$H NMR (500 MHz, Chloroform) d=8.16 (d, J=8.2 Hz, 1H), 7.83 (d, J=8.2 Hz, 1H), 5.29 (s, 2H), 4.46 (q, J=7.2 Hz, 2H), 3.20 (s, 2.65H), 3.10 (s, 0.35H), 2.91 (s, 2.65H), 2.79 (s, 0.35H), 2.66 (s, 0.35H), 2.45 (s, 2.65H), 1.43 (t, J=7.1 Hz, 3H).

To a solution of ethyl 2-chloro-3-[[[N-cyano-C-methyl-carbonimidoyl]-methyl-amino]methyl]-4-methylsulfonyl-benzoate (77 mg, 0.19 mmol) in THF (2 mL) and water (2 mL) was added lithium hydroxide monohydrate (24 mg, 0.56 mmol). The reaction was stirred at room temperature for 30 min. The mixture was acidified with 2 N HCl to pH ~2. The mixture was extracted with EtOAc (×3), reacidifying the aqueous layer on each occassion to maintain pH ~2. The combined organics were dried by passing through a phase separator, and then concentrated in vacuo. 2-chloro-3-[[[N-cyano-C-methyl-carbonimidoyl]-methyl-amino]methyl]-4-methylsulfonyl-benzoic acid (51 mg, 0.14 mmol) as a solid.

A solution of 2-chloro-3-[[[(Z)—N-cyano-C-methyl-carbonimidoyl]-methyl-amino]methyl]-4-methylsulfonyl-benzoic acid (54 mg, 0.16 mmol), 1-methyl-H-tetrazol-5-amine (0.20 mmol, 21 mg) and DMAP (0.47 mmol, 58 mg) in $CH_2Cl_2$ (1.5 mL) were stirred at RT for 1 h. Propylphosphonic anhydride (50% wt. in ethyl acetate, 0.94 mmol, 0.56 mL) was added to the reaction mixture, and was transferred to a microwave vial and heated in the microwave to 100° C. for 30 min. The reaction mixture was concentrated in vacuo to give an orange oil, and then was dissolved in EtOAc (25 mL). The organic was washed with water (carefully acidified to pH ~4), and the aqueous further extracted with EtOAc (×2). The combined organics were washed with brine, dried over magnesium sulfate and concentrated in vacuo. The residue was purified by reversed-phase prep HPLC to give 2-chloro-3-[[[(Z)—N-cyano-C-methyl-carbonimidoyl]-methyl-amino]methyl]-4-methylsulfonyl-N-(1-methyltetrazol-5-yl)benzamide (8.5 mg, 0.018 mmol) as a colourless oil. NMR analysis showed the desired product exists as a mixture of isomers (~2:1, not assigned). 1H NMR (400 MHz, Methanol) d=8.29-8.22 (m, 1H), 7.99-7.88 (m, 1H), 5.37 (s, 2H), 4.06 (s, 3H), 3.93 (s, 1H), 2.95 (s, 2H), 2.83-2.78 (m, 1H), 2.68-2.65 (m, 1H), 2.47 (s, 2H). NOTE: 2H not observed (masked by residual methanol peak at 3.30 ppm).

PREPARATIVE EXAMPLE 5: COMPOUND 2.049

Oxalyl dichloride (0.67 g, 0.46 mL, 5.2 mmol) was added dropwise to a solution of N,N-dimethylformamide (0.20 mL, 2.6 mmol) in dichloromethane (3.8 mL) at 0° C. Vigorous effervescence was observed then a white suspension formed. The reaction mixture was allowed to stir for 30 min at room temperature and was then concentrated to dryness giving an off-white solid. This solid was suspended in dichloromethane (5 mL) and then ethyl 3-amino-2-chloro-4-(trifluoromethyl)benzoate (350 mg, 1.31 mmol) was added as a solution in dichloromethane (2 mL). Within a few seconds a yellow solution formed, which was stirred for 10 min. The reaction mixture was added dropwise to stirring sat. $NaHCO_3$ solution in an ice bath and stirred for 10 mins (care: effervescence). The organic layer was separated, extracted again with dichloromethane (10 mL), then $CHCl_3$:IPA (7:3 ratio, 10 mL) then the combined organic layers were dried ($MgSO_4$) and concentrated in vacuo. The material was loaded onto celite and purified by flash chromatography. Column: 24 g silica. Solvent A: isohexane. Solvent B: Ethyl acetate. Gradient: 0-50% B in A over 15 min. The fractions containing the product were combined and concentrated in vacuo to give ethyl 2-chloro-3-[(E)-dimethyl-aminomethyleneamino]-4-(trifluoromethyl) benzoate (319 mg, 0.989 mmol) as a yellow oil. 1H NMR (400 MHz, chloroform) δ=7.50 (d, J=8.2 Hz, 1H), 7.34-7.28 (m, 2H), 4.41 (q, J=7.1 Hz, 2H), 3.05 (br d, J=8.8 Hz, 6H), 1.40 (t, J=7.2 Hz, 3H).

To a stirred solution of ethyl 2-chloro-3-[(E)-dimethyl-aminomethyleneamino]-4-(trifluoro methyl)benzoate (300 mg, 0.930 mmol), in ethanol (5 mL) and water (1.5 mL) was added lithium hydroxide monohydrate (98 mg, 2.3 mmol). After stirring at RT for 2 h, The mixture was concentrated in vacuo. The material was taken up in water (10 mL) and the aqueous solution was adjusted to pH 10 by addition of excess ammonia solution (38% in water). This was directly purified by reversed phase flash chromatography: Column: C-18 aq (50 g). Solvent A: Water+0.1% ammonia. Solvent B: acetonitrile+0.1% ammonia. Gradient: 0% for 3 column volumes, then 0-50% B in A over 10 column volumes. Eluted at 5% B in A. The desired fractions were concentrated and freeze-dried to afford 2-chloro-3-[(E)-dimethylaminomethyleneamino]-4-(trifluoromethyl)benzoic acid (280 mg, 274 mmol) as a white solid. 1H NMR (400 MHz, DMSO-d6) δ=7.42 (s, 1H), 7.34 (d, J=8.1 Hz, 1H), 6.85 (d, J=7.9 Hz, 1H), 3.05-2.87 (m, 6H).

To a flask containing 2-chloro-3-[(E)-dimethylaminomethyleneamino]-4-(trifluoromethyl) benzoic acid (270 mg, 0.916 mmol) was added anhydrous 1,4-dioxane (8 mL) and N,N'-carbonyldiimidazole (223 mg, 1.37 mmol). DBU (0.140 mL, 0.916 mmol) and 5-methyl-1,3,4-oxadiazol-2-amine (136 mg, 1.37 mmol) were added and the mixture heated at 100° C. for 16 h. The material was cooled to RT and concentrated in vacuo. Saturated sodium bicarbomate (10 mL) and DCM (10 mL) were added and the layers were separated. The aqueous layer was extracted with DCM (10 mL) and $CHCl_3$:IPA (7:3, 10 mL). The combined organic layers were dried over $MgSO_4$, filtered and concentrated in vacuo. The material was loaded onto celite and purified by flash chromatography: 24 g silica. Solvent A: Dichloromethane. Solvent B: Methanol. Gradient: 0-10% B in A over 25 min. The fractions containing the product were combined and concentrated in vacuo to give 2-chloro-3-[(E)-dimethylaminomethyleneamino]-N-(5-methyl-1,3,4-oxadiazol-2-yl)-4-(trifluoromethyl)benzamide (75 mg, 0.20 mmol) as a white solid. $^1H$ NMR (400 MHz, DMSO-$d_6$) δ=7.60-7.50 (m, 2H), 7.18-7.11 (m, 1H), 3.02 (s, 3H), 2.98-2.90 (m, 3H), 2.46-2.33 (m, 3H).

PREPARATIVE EXAMPLE 6: COMPOUND 3.129

To a dry flask was added ethyl 3-(bromomethyl)-2-chloro-4-methylsulfonyl-benzoate (2.7 g, 7.6 mmol), potassium carbonate (1.g g, 9.1 mmol) and anhydrous acetonitrile (41 mL). The reaction mixture was purged and put under a nitrogen atmosphere. A suspension of N'-hydroxy-N,N-dimethyl-acetamidine (0.85 g, 8.4 mmol) in anhydrous acetonitrile (20 mL) was added to the reaction mixture dropwise and the reaction mixture was stirred at room temperature for 13 days. A further portion of N'-hydroxy-N,N-dimethyl-acetamidine (0.16 g, 1.5 mmol) and potassium carbonate (0.21 g, 1.5 mmol) were added and the reaction mixture was stirred at RT for a further day. The reaction mixture was diluted with dichloromethane (50 mL) and water (10 mL) was added to the reaction mixture. The phases were separated and the organic phase was passed through a phase separation cartridge and concentrated in vacuo to give a yellow oil. The crude material was purified by flash chromatography (Solvent A=hexane, Solvent B=ethyl acetate) gradient 0-50% ethyl acetate to give the desired product ethyl 2-chloro-3-[[(Z)-1-(dimethylamino)ethylideneamino]oxymethyl]-4-methylsulfonyl-benzoate (1.56 g, 4.13 mmol) as a yellow oil. 1H NMR (400 MHz, chloroform) δ=8.11 (d, J=8.3 Hz, 1H), 7.73 (d, J=8.3 Hz, 1H), 5.56 (s, 2H), 4.55-4.33 (m, 2H), 3.39 (s, 3H), 2.73 (s, 6H), 1.94 (s, 3H), 1.42 (t, J=7.2 Hz, 3H).

To a stirred solution of ethyl 2-chloro-3-[[(Z)-1-(dimethylamino)ethylideneamino]oxymethyl]-4-methylsulfonyl-benzoate (1.5 g, 4.0 mmol) in ethanol (23 mL) and water (6.4 mL) was added lithium hydroxide monohydrate (0.42 g, 9.9 mmol) was added to the reaction mixture and it was stirred at room temperature for 16 h. The reaction mixture was concentrated in vacuo to remove the ethanol. The crude material was acidified with 2 N HCl to pH 3 and then aqueous ammonia was added until the pH was pH 10. This mixture was loaded onto a reverse phase column (high pH) that had been equilibrated with a solution of 0.1% ammonia in water and acetonitrile. The sample was loaded as a liquid onto the equilibrated column and was eluted using 0% acetonitrile in water (0.1% NH3) until solvent front came off, then a gradient from 0%-50% acetonitrile in water (0.1% NH3) until product eluted (approx 30%). The material was taken up in minimum amount of water and very small amount of acetonitrile and freeze dried overnight. The product 2-chloro-3-[[(Z)-1-(dimethylamino)ethylideneamino]oxymethyl]-4-methylsulfonyl-benzoic acid (1.31 g, 3.76 mmol) was obtained as an off-white solid. 1H NMR (400 MHz, DMSO-d6) δ=7.84 (d, J=8.1 Hz, 1H), 7.43 (d, J=8.1 Hz, 1H), 7.36-7.21 (m, 1H), 5.35 (s, 2H), 3.37 (s, 3H), 2.69 (s, 6H), 1.88 (s, 3H).

To a solution of 2-chloro-3-[[(Z)-1-(dimethylamino)ethylideneamino]oxymethyl]-4-methyl sulfonyl-benzoic acid (500 mg, 1.43 mmol), in dichloromethane (7.5 mL) was added DMF (0.011 mL, 0.14 mmol). The reaction mixture was purged and put under a nitrogen atmosphere. Oxalyl chloride (0.24 mL, 0.96 mmol) was added dropwise; effervescence occurred on addition, and a red solid precipitate appeared. The reaction mixture was stirred at room temperature for 1 h and it became a pinkish red suspension. The reaction mixture was concentrated in vacuo to give a pink foaming solid, and the residue was dissolved in dichloromethane (7.5 mL). The reaction mixture was cooled to 0° C. under a nitrogen atmosphere and after 5 min, triethylamine (0.81 mL, 0.734 mmol) was added dropwise, followed by cyclohexane-1,3-dione (161 mg, 1.43 mmol) in a single portion. The reaction mixture was allowed to warm to RT over 1 h. Acetone cyanohydrin (0.33 mL, 0.36 mmol) was added to the reaction mixture. The reaction mixture was stirred at room temperature overnight. The reaction mixture was concentrated in vacuo and then the crude material was loaded onto celite and purified by flash chromatography using a solvent system of 10:4:2:2:0.5 toluene/1,4-dioxane/ethanol triethylamine/water. The crude material (dark green oil) was diluted with dichloromethane (10 mL) and washed with 10% w/v citric acid solution (10 mL). The organic phase was dried over MgSO₄, filtered and concentrated in vacuo to give N'-[[2-chloro-3-(2,6-dioxocyclohexanecarbonyl)-6-methylsulfonyl-phenyl]methoxy]-N,N-dimethyl-acetamidine (114 mg, 0.527 mmol) as a yellow oil (114 mg). 1H NMR (CDCl₃): 8.12 (d, J=8.1 Hz, 1H), 5.54 (s, 2H), 3.37 (s, 3H), 2.81 (t, J=6.4 Hz, 2H), 2.73 (s, 6H), 2.44 (t, J=6.4 Hz, 2H), 2.13-2.02 (m, 2H), 1.92 (s, 3H).

PREPARATIVE EXAMPLE 7: COMPOUND 4.016

To a solution of methylamine (2 M in THF, 55 mL, 109 mmol) was added dropwise ethyl 3-(bromomethyl)-2-chloro-4-methylsulfonyl-benzoate (2.43 g, 6.83 mmol) in acetonitrile (13.7 mL). The reaction was stirred at room temperature for 10 min. LCMS analysis showed formation of the product and no remaining starting material. The reaction was concentrated in vacuo and then diluted with DCM (250 mL). The organic was washed with sat. K2CO3 solution (100 mL), brine (100 mL), and concentrated in vacuo to give ethyl 2-chloro-3-(methylaminomethyl)-4-methylsulfonyl-benzoate (2.08 g, 6.46 mmol) as a colourless oil. 1H NMR (400 MHz, chloroform) 6=8.10 (d, J=8.2 Hz, 1H), 7.71 (d, J=8.3 Hz, 1H), 4.44 (q, J=7.1 Hz, 2H), 4.33 (s, 2H), 3.37 (s, 3H), 2.55 (s, 3H), 1.42 (t, J=7.1 Hz, 3H).

To a solution of ethyl 2-chloro-3-(methylaminomethyl)-4-methylsulfonyl-benzoate (500 mg, 1.55 mmol), 4-dimethylaminopyridine (19.4 mg, 0.155 mmol) and triethylamine (318 mg, 0.437 mL, 3.11 mmol) in tetrahydrofuran (13.8 g, 15.5 mL) was added dropwise ethyl dithioacetate (381 mg, 0.364 mL, 3.11 mmol). The reaction was equipped with a reflux condenser, stirred and heated to 50° C. for 10 days. LCMS analysis showed formation of product, but also remaining starting material. The reaction was cooled to room temperature, and then concentrated in vacuo to remove THF. The mixture was diluted with EtOAc (50 mL) and washed with water (50 mL×2), brine (50 mL) and concentrated in vacuo. The product was purified by flash column chromatography (0-60% EtOAc/isohexane) to give ethyl 2-chloro-3-[[ethanethioyl(methyl)amino]methyl]-4-methylsulfonyl-benzoate (217 mg, 0.596 mmol) as a brown gum. 1H NMR (400 MHz, chloroform) 6=8.23-8.14 (m, 1H), 7.89-7.80 (m, 1H), 5.79 (br s, 2H), 4.46 (q, J=7.2 Hz, 2H), 3.20 (s, 2.6H), 3.15 (s, 0.4H), 3.10 (s, 0.4H), 2.99 (s, 2.6H), 2.94-2.91 (m, 0.4H), 2.71 (s, 2.6H), 1.42 (t, J=7.2 Hz, 3H).

To a solution of ethyl 2-chloro-3-[[ethanethioyl(methyl)amino]methyl]-4-methylsulfonyl-benzoate (120 mg, 0.330 mmol) in acetonitrile (3.89 g, 4.95 mL, 94.2 mmol) was added triethylamine (337 mg, 0.464 mL, 3.30 mmol), o-methylhydroxylamine hydrochloride (141 mg, 1.65 mmol) and silver tetrafluoroborate (0.3242 g, 1.65 mmol). The reaction mixture was stirred overnight at room temperature. LCMS analysis showed formation of product and no remaining starting material. The solution was filtered through a plug of silica to remove the silver precipitate, and washed with MeCN (20 mL). The mixture was concentrated in vacuo to remove the MeCN. The residue was dissolved in EtOAc (20 mL) and washed with water (20 mL), brine (20 mL), dried over magnesium sulfate and concentrated in vacuo. The product was purified by flash column chromatography (0-50% EtOAc/isohexane) to give ethyl 2-chloro-3-[[[N-methoxy-C-methyl-carbonimidoyl]-methyl-amino]methyl]-4-methylsulfonyl-benzoate (90 mg, 0.239 mmol) as a brown gum. 1H NMR (400 MHz, chloroform) 6=8.13 (d, J=8.2 Hz, 1H), 7.70 (d, J=8.2 Hz, 1H), 4.94 (s, 2H), 4.45 (q, J=7.2 Hz, 2H), 3.71 (s, 3H), 3.20 (s, 3H), 2.61 (s, 3H), 2.05 (s, 3H), 1.42 (t, J=7.2 Hz, 3H).

To a solution of ethyl 2-chloro-3-[[[N-methoxy-C-methyl-carbonimidoyl]-methyl-amino]methyl]-4-methylsulfonyl-benzoate (95 mg, 0.252 mmol) in tetrahydrofuran (1.69 g, 1.90 mL, 23.4 mmol) and water (1.9 g, 1.9 mL, 0.106 mmol) was added lithium hydroxide (53.9 mg, 2.25 mmol). The reaction was stirred at room temperature for 30 min. LCMS analysis showed formation of product. The mixture was partly concentrated in vacuo to remove tetrahydrofuran. The resulting aqueous solution was diluted with water (1 mL) and acidified with a few drops of 2 M HCl to pH 2. The mixture was then basified with aqueous NH₃ until pH 9. The resulting solution was loaded on to a reverse phase column and purified using reverse phase chromatography (0-20% MeCN in H₂O containing 0.1% NH₃). The column fractions containing product were combined and concentrated using a freeze-dryer over the weekend to give 2-chloro-3-[[[N-methoxy-C-methyl-carbonimidoyl]- methyl-amino]methyl]-4-methylsulfonyl-benzoic acid (84 mg, 0.229 mmol) as a yellow gum.

A solution of 2-chloro-3-[[[N-methoxy-C-methyl-carbonimidoyl]-methyl-amino]methyl]-4-methylsulfonyl-benzoic acid (65 mg, 0.186 mmol), 1-methyl-1H-tetrazol-5-amine (25.3 mg, 0.242 mmol) and 4-dimethylaminopyridine (69.0 mg, 0.559 mmol) in DCM (2.47 g, 1.86 mL, 29.0 mmol) were stirred at room temperature for 1 h. 1-propanephosphonic anhydride (0.712 g, 0.666 mL, 1.12 mmol) was added to the reaction mixture, and was transferred to a microwave vial and heated in the microwave to 100° C. for 30 min. LCMS analysis showed formation of product. The reaction mixture was concentrated in vacuo to give an orange oil. The solution was diluted in water (5 mL) and basified with conc. NH3 solution until pH ~9/10. The product was purified by reverse phase column chromatography (0-50% MeCN in $H_2O$ containing 0.1% $NH_3$). The product containing fractions were concentrated using the freeze-dryer to give 2-chloro-3-[[[N-methoxy-C-methyl-carbonimidoyl]-methyl-amino]methyl]-4-methylsulfonyl-N-(1-methyltetrazol-5-yl)benzamide (8.3 mg, 0.019 mmol) as a colourless gum. $^1$H NMR (400 MHz, methanol) δ=8.20 (d, J=8.2 Hz, 1H), 7.83 (d, J=8.1 Hz, 1H), 4.95 (s, 2H), 4.06 (s, 3H), 3.68 (s, 3H), 3.27 (s, 3H), 2.60 (s, 3H), 2.06 (s, 3H).

PREPARATIVE EXAMPLE 8: COMPOUND 5.014

To a solution of methylamine (2 M in THF, 40 g, 46 mL, 92.6 mmol) was added dropwise ethyl 3-(bromomethyl)-2-chloro-4-(trifluoromethyl)benzoate (2.0 g, 5.79 mmol) in acetonitrile (11.6 mL). The reaction was stirred at room temperature for 10 min. LCMS analysis showed formation of product and no remaining starting material. The reaction was concentrated in vacuo, then diluted with EtOAc (200 mL) and washed with sat. $K_2CO_3$ solution (100 mL), brine (100 mL) and concentrated in vacuo to give ethyl 2-chloro-3-(methylaminomethyl)-4-(trifluoromethyl)benzoate (1.80 g, 5.78 mmol) as a yellow oil. NMR analysis showed the desired product. $^1$H NMR (400 MHz, chloroform) δ=7.73-7.53 (m, 2H), 4.43 (q, J=7.1 Hz, 2H), 4.01 (d, J=0.7 Hz, 2H), 2.51 (s, 3H), 1.41 (t, J=7.1 Hz, 3H) (N—H not observed). $^{19}$F NMR (376 MHz, chloroform) δ= −58.94

To a solution of ethyl 2-chloro-3-(methylaminomethyl)-4-(trifluoromethyl)benzoate (500 mg, 1.69 mmol), 4-dimethylaminopyridine (21.1 mg, 0.169 mmol) and triethylamine (346 mg, 0.476 mL, 3.38 mmol) in tetrahydrofuran (15.0 g, 16.9 mL) was added dropwise ethyl dithioacetate (415 mg, 0.396 mL, 3.38 mmol). The reaction was equipped with a reflux condenser, stirred and heated to 60° C. for 10 days. LCMS analysis showed formation of product, but also remaining starting material. The reaction was cooled to room temperature, and then concentrated in vacuo to remove tetrahydrofuran. The mixture was diluted with DCM (50 mL) and water (50 mL). The water was extracted with DCM (50 mL×2), and then the organics washed with brine (50 mL), and concentrated in vacuo. The product was purified by flash column chromatography (0-30% EtOAc/isohexane) to give ethyl 2-chloro-3-[[ethanethioyl(methyl)amino]methyl]-4-(trifluoromethyl)benzoate (370 mg, 0.941 mmol) as a brown gum. NMR shows two rotamers. $^1$H NMR (400 MHz, chloroform) δ=7.87-7.71 (m, 2H), 5.54 (br s, 1.5H), 5.09 (s, 0.5H), 4.50-4.39 (m, 2H), 3.09 (s, 0.75H), 2.89 (s, 3H), 2.72 (s, 2.25H), 1.46-1.37 (m, 3H).

To a solution of ethyl 2-chloro-3-[[ethanethioyl(methyl)amino]methyl]-4-(trifluoromethyl)benzoate (370 mg, 1.05 mmol) in acetonitrile (12.3 g, 15.7 mL) was added triethylamine (1.07 g, 1.47 mL, 10.46 mmol), O-methylhydroxylamine hydrochloride (446 mg, 5.23 mmol) and silver tetrafluoroborate (1.03 g, 5.23 mmol). The reaction mixture was stirred for 5 days at room temperature. LCMS analysis showed formation of product and no remaining starting material. The solution was filtered through a plug of silica to remove the silver precipitate, and washed with MeCN (20 mL). The mixture was concentrated in vacuo to remove the MeCN. The residue was dissolved in EtOAc (20 mL) and washed with water (20 mL), brine (20 mL), dried over magnesium sulfate and concentrated in vacuo. The product was purified by flash column chromatography (0-20% EtOAc/isohexane) to give ethyl 2-chloro-3-[[[(Z)—N-methoxy-C-methyl-carbonimidoyl]-methyl-amino]methyl]-4-(trifluoromethyl)benzoate (254 mg, 0.692 mmol) as a brown gum. $^1$H NMR (400 MHz, chloroform) δ=7.67 (s, 2H), 4.66 (d, J=0.9 Hz, 2H), 4.44 (q, J=7.2 Hz, 2H), 3.74 (s, 3H), 2.48 (s, 3H), 2.04 (s, 3H), 1.41 (t, J=7.2 Hz, 3H). $^{19}$F NMR (376 MHz, chloroform) d= −58.33 (s, 1F).

To a solution of ethyl 2-chloro-3-[[[N-methoxy-C-methyl-carbonimidoyl]-methyl-amino]methyl]-4-(trifluoromethyl)benzoate (250 mg, 0.682 mmol) in tetrahydrofuran (4.45 g, 5.0 mL, 61.6 mmol) and water (5.0 g, 5.0 mL, 277 mmol) was added lithium hydroxide (87.4 mg, 2.05 mmol). The reaction was stirred at room temperature for 3 h. LCMS analysis showed formation of product. The resulting aqueous solution was diluted with water (1 mL) and acidified with a few drops of 2 M HCl to pH ~2. The mixture was then concentrated in vacuo to remove THF and most of the water. The mixture was then diluted with water (2 mL total) and basified with aqueous $NH_3$ until pH 9. The resulting solution was loaded on to a reverse phase column and purified using reverse phase chromatography (0-20% MeCN in $H_2O$ containing 0.1% $NH_3$). The product containing fractions were concentrated using a freeze dryer overnight to give 2-chloro-3-[[[N-methoxy-C-methyl-carbonimidoyl]-methyl-amino]methyl]-4-(trifluoromethyl)benzoic acid (207 mg, 0.580 mmol).

A solution of 2-chloro-3-[[[N-methoxy-C-methyl-carbonimidoyl]-methyl-amino]methyl]-4-(trifluoromethyl)benzoic acid (75 mg, 0.221 mmol), 5-methyl-1,3,4-oxadiazol-2-amine (29.4 mg, 0.287 mmol) and 4-dimethylaminopyridine (82.0 mg, 0.665 mmol) in DCM (2.93 g, 2.21 mL, 34.5 mmol) were stirred at room temperature for 1 h. 1-propanephosphonic anhydride (846 mg, 0.791 mL, 1.33 mmol) was added to the reaction mixture, and was transferred to a microwave vial and heated in the microwave to 80° C. for 1 h. LCMS analysis showed formation of product. The reaction mixture was concentrated in vacuo to give an orange oil. The mixture was dissolved in DCM (20 mL), and partitioned with dilute $NaHCO_3$ (20 mL). The aqueous was washed with DCM (20 mL×5). The combined organics were washed with brine (20 mL) and concentrated in vacuo. The product was purified to give 2-chloro-3-[[[N-methoxy-C-methyl-carbonimidoyl]-methyl-amino]methyl]-N-(5-methyl-1,3,4-oxadiazol-2-yl)-4-(trifluoromethyl)benzamide (4.0 mg, 9.53 µmol) as a colourless gum. $^1$H NMR (400 MHz, Methanol) δ=7.83 (d, J=8.1 Hz, 1H), 7.68 (d, J=8.1 Hz, 1H), 4.65 (s, 2H), 3.68 (s, 3H), 2.55-2.44 (m 6H), 2.04 (s, 3H).

TABLE 1

Examples of herbicidal compounds of the present invention.

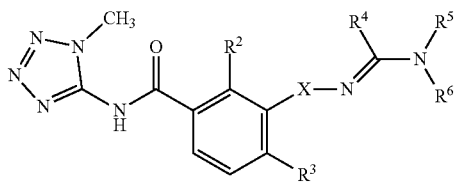

| Compound Number | R² | R³ | R⁴ | R⁵ | R⁶ | X | 1H-NMR (in CDCl₃ unless otherwise stated) |
|---|---|---|---|---|---|---|---|
| 1.001 | Me | Me | H | Me | Me | — | |
| 1.002 | Me | Me | H | Me | Me | CH₂ | |
| 1.003 | Me | Me | H | Me | Et | — | |
| 1.004 | Me | Me | H | Me | Et | CH₂ | |
| 1.005 | Me | Me | H | Et | Me | — | |
| 1.006 | Me | Me | H | Et | Me | CH₂ | |
| 1.007 | Me | Me | H | Et | Et | — | |
| 1.008 | Me | Me | H | Et | Et | CH₂ | |
| 1.009 | Me | Cl | H | Me | Me | — | |
| 1.010 | Me | Cl | H | Me | Me | CH₂ | |
| 1.011 | Me | Cl | H | Me | Et | — | |
| 1.012 | Me | Cl | H | Me | Et | CH₂ | |
| 1.013 | Me | Cl | H | Et | Me | — | |
| 1.014 | Me | Cl | H | Et | Me | CH₂ | |
| 1.015 | Me | Cl | H | Et | Et | — | |
| 1.016 | Me | Cl | H | Et | Et | CH₂ | |
| 1.017 | Me | CF₃ | H | Me | Me | — | 1HNMR (400 MHz, d4-methanol) 7.57 (d, 1H), 7.36 (d, 1H), 7.29 (d, 1H), 4.05 (s, 3H), 3.05 (s, 6H), 2.27 (s, 3H) |
| 1.018 | Me | CF₃ | H | Me | Me | CH₂ | |
| 1.019 | Me | CF₃ | H | Me | Et | — | |
| 1.020 | Me | CF₃ | H | Me | Et | CH₂ | |
| 1.021 | Me | CF₃ | H | Et | Me | — | |
| 1.022 | Me | CF₃ | H | Et | Me | CH₂ | |
| 1.023 | Me | CF₃ | H | Et | Et | — | |
| 1.024 | Me | CF₃ | H | Et | Et | CH₂ | |
| 1.025 | Me | SO₂Me | H | Me | Me | — | 1H NMR (400 MHz, DMSO-d6) d = 7.71 (d, J = 8.2 Hz, 1H), 7.39 (s, 1H), 7.30 (d, J = 8.2 Hz, 1H), 3.88 (s, 3H), 3.24 (s, 3H), 3.00 (s, 6H), 2.18 (s, 3H) |
| 1.026 | Me | SO₂Me | H | Me | Me | CH₂ | |
| 1.027 | Me | SO₂Me | H | Me | Et | — | 1HNMR (400 MHz, chloroform): 10.76 (brs, 1H), 7.87 (d, 1H), 7.42-7.31 (m, 1.7H), 4.10 (s, 3H), 3.61-3.52 (m, 0.7H), 3.33 (q, 1.3H), 3.22 (s, 3H), 3.06 (s, 2H), 3.03 (s, 1H), 2.32 (s, 3H), 1.25 (q, 3H) |
| 1.028 | Me | SO₂Me | H | Me | Et | CH₂ | |
| 1.029 | Me | SO₂Me | H | Et | Me | — | |
| 1.030 | Me | SO₂Me | H | Et | Me | CH₂ | |
| 1.031 | Me | SO₂Me | H | Et | Et | — | 1HNMR (400 MHz, chloroform): 11.21-10.14 (m, 1H), 7.87 (d, 1H), 7.36 (d, 1H), 7.31 (s, 1H), 4.10 (s, 3H), 3.56 (q, 2H), 3.31 (q, 2H), 3.21 (s, 3H), 2.33 (s, 3H), 1.33-1.21 (m, 6H) |
| 1.032 | Me | SO₂Me | H | Et | Et | CH₂ | |
| 1.033 | Cl | Me | H | Me | Me | — | |
| 1.034 | Cl | Me | H | Me | Me | CH₂ | |
| 1.035 | Cl | Me | H | Me | Et | — | |
| 1.036 | Cl | Me | H | Me | Et | CH₂ | |
| 1.037 | Cl | Me | H | Et | Me | — | |
| 1.038 | Cl | Me | H | Et | Me | CH₂ | |
| 1.039 | Cl | Me | H | Et | Et | — | |
| 1.040 | Cl | Me | H | Et | Et | CH₂ | |
| 1.041 | Cl | Cl | H | Me | Me | — | 1H NMR (400 MHz, DMSO-d6) δ = 12.13-11.48 (m, 1H), 7.59 (s, 1H), 7.51 (d, J = 8.3 Hz, 1H), 7.23 (d, J = 8.3 Hz, 1H), 3.97 (s, 3H), 3.06-2.96 (m, 6H) |
| 1.042 | Cl | Cl | H | Me | Me | CH₂ | |
| 1.043 | Cl | Cl | H | Me | Et | — | |
| 1.044 | Cl | Cl | H | Me | Et | CH₂ | |
| 1.045 | Cl | Cl | H | Et | Me | — | |
| 1.046 | Cl | Cl | H | Et | Me | CH₂ | |

TABLE 1-continued

Examples of herbicidal compounds of the present invention.

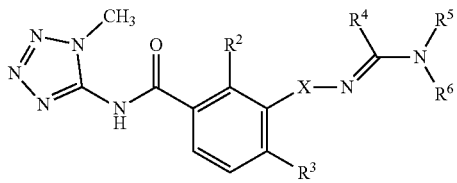

| Compound Number | R² | R³ | R⁴ | R⁵ | R⁶ | X | 1H-NMR (in CDCl₃ unless otherwise stated) |
|---|---|---|---|---|---|---|---|
| 1.047 | Cl | Cl | H | Et | Et | — | |
| 1.048 | Cl | Cl | H | Et | Et | CH₂ | |
| 1.049 | Cl | CF₃ | H | Me | Me | — | 1H NMR (400 MHz, DMSO-d6) δ = 11.86 (br s, 1H), 7.83-7.59 (m, 2H), 7.55-7.33 (m, 1H), 4.00 (s, 3H), 3.07 (br s, 3H), 2.99 (br s, 3H) |
| 1.050 | Cl | CF₃ | H | Me | Me | CH₂ | |
| 1.051 | Cl | CF₃ | H | Me | Et | — | |
| 1.052 | Cl | CF₃ | H | Me | Et | CH₂ | |
| 1.053 | Cl | CF₃ | H | Et | Me | — | |
| 1.054 | Cl | CF₃ | H | Et | Me | CH₂ | |
| 1.055 | Cl | CF₃ | H | Et | Et | — | δ = 10.42 (br s, 1H), 7.60 (d, J = 8.2 Hz, 1H), 7.36 (s, 1H), 7.31 (d, J = 8.1 Hz, 1H), 4.12 (s, 3H), 3.54 (q, J = 7.1 Hz, 2H), 3.31 (q, J = 7.2 Hz, 2H), 1.29-1.23 (m, 6H) |
| 1.056 | Cl | CF₃ | H | Et | Et | CH₂ | |
| 1.057 | Cl | SO₂Me | H | Me | Me | — | 1HNMR (400 MHz, DMSO-d6): 3.05 (d, 6H), 3.33 (s, 3H), 3.98 (s, 3H), 7.41 (d, 1H), 7.62 (s, 1H), 7.87 (d, 1H) |
| 1.058 | Cl | SO₂Me | H | Me | Me | CH₂ | |
| 1.059 | Cl | SO₂Me | H | Me | Et | — | |
| 1.060 | Cl | SO₂Me | H | Me | Et | CH₂ | |
| 1.061 | Cl | SO₂Me | H | Et | Me | — | |
| 1.062 | Cl | SO₂Me | H | Et | Me | CH₂ | |
| 1.063 | Cl | SO₂Me | H | Et | Et | — | |
| 1.064 | Cl | SO₂Me | H | Et | Et | CH₂ | |
| 1.065 | CF₃ | Me | H | Me | Me | — | |
| 1.066 | CF₃ | Me | H | Me | Me | CH₂ | |
| 1.067 | CF₃ | Me | H | Me | Et | — | |
| 1.068 | CF₃ | Me | H | Me | Et | CH₂ | |
| 1.069 | CF₃ | Me | H | Et | Me | — | |
| 1.070 | CF₃ | Me | H | Et | Me | CH₂ | |
| 1.071 | CF₃ | Me | H | Et | Et | — | |
| 1.072 | CF₃ | Me | H | Et | Et | CH₂ | |
| 1.073 | CF₃ | Cl | H | Me | Me | — | |
| 1.074 | CF₃ | Cl | H | Me | Me | CH₂ | |
| 1.075 | CF₃ | Cl | H | Me | Et | — | |
| 1.076 | CF₃ | Cl | H | Me | Et | CH₂ | |
| 1.077 | CF₃ | Cl | H | Et | Me | — | |
| 1.078 | CF₃ | Cl | H | Et | Me | CH₂ | |
| 1.079 | CF₃ | Cl | H | Et | Et | — | |
| 1.080 | CF₃ | Cl | H | Et | Et | CH₂ | |
| 1.081 | CF₃ | CF₃ | H | Me | Me | — | |
| 1.082 | CF₃ | CF₃ | H | Me | Me | CH₂ | |
| 1.083 | CF₃ | CF₃ | H | Me | Et | — | |
| 1.084 | CF₃ | CF₃ | H | Me | Et | CH₂ | |
| 1.085 | CF₃ | CF₃ | H | Et | Me | — | |
| 1.086 | CF₃ | CF₃ | H | Et | Me | CH₂ | |
| 1.087 | CF₃ | CF₃ | H | Et | Et | — | |
| 1.088 | CF₃ | CF₃ | H | Et | Et | CH₂ | |
| 1.089 | CF₃ | SO₂Me | H | Me | Me | — | 1HNMR (500 MHz, Chloroform): 8.23 (d, 1H), 7.36 (s, 1H), 7.24 (d, 1H), 4.11 (s, 3H), 3.27 (s, 3H), 3.07 (d, 6H) |
| 1.090 | CF₃ | SO₂Me | H | Me | Me | CH₂ | |
| 1.091 | CF₃ | SO₂Me | H | Me | Et | — | |
| 1.092 | CF₃ | SO₂Me | H | Me | Et | CH₂ | |
| 1.093 | CF₃ | SO₂Me | H | Et | Me | — | |
| 1.094 | CF₃ | SO₂Me | H | Et | Me | CH₂ | |
| 1.095 | CF₃ | SO₂Me | H | Et | Et | — | |
| 1.096 | CF₃ | SO₂Me | H | Et | Et | CH₂ | |
| 1.097 | SO₂Me | Me | H | Me | Me | — | |
| 1.098 | SO₂Me | Me | H | Me | Me | CH₂ | |
| 1.099 | SO₂Me | Me | H | Me | Et | — | |
| 1.100 | SO₂Me | Me | H | Me | Et | CH₂ | |

TABLE 1-continued

Examples of herbicidal compounds of the present invention.

| Compound Number | R² | R³ | R⁴ | R⁵ | R⁶ | X | 1H-NMR (in CDCl₃ unless otherwise stated) |
|---|---|---|---|---|---|---|---|
| 1.101 | SO₂Me | Me | H | Et | Me | — | |
| 1.102 | SO₂Me | Me | H | Et | Me | CH₂ | |
| 1.103 | SO₂Me | Me | H | Et | Et | — | |
| 1.104 | SO₂Me | Me | H | Et | Et | CH₂ | |
| 1.105 | SO₂Me | Cl | H | Me | Me | — | |
| 1.106 | SO₂Me | Cl | H | Me | Me | CH₂ | |
| 1.107 | SO₂Me | Cl | H | Me | Et | — | |
| 1.108 | SO₂Me | Cl | H | Me | Et | CH₂ | |
| 1.109 | SO₂Me | Cl | H | Et | Me | — | |
| 1.110 | SO₂Me | Cl | H | Et | Me | CH₂ | |
| 1.111 | SO₂Me | Cl | H | Et | Et | — | |
| 1.112 | SO₂Me | Cl | H | Et | Et | CH₂ | |
| 1.113 | SO₂Me | CF₃ | H | Me | Me | — | |
| 1.114 | SO₂Me | CF₃ | H | Me | Me | CH₂ | |
| 1.115 | SO₂Me | CF₃ | H | Me | Et | — | |
| 1.116 | SO₂Me | CF₃ | H | Me | Et | CH₂ | |
| 1.117 | SO₂Me | CF₃ | H | Et | Me | — | |
| 1.118 | SO₂Me | CF₃ | H | Et | Me | CH₂ | |
| 1.119 | SO₂Me | CF₃ | H | Et | Et | — | |
| 1.120 | SO₂Me | CF₃ | H | Et | Et | CH₂ | |
| 1.121 | SO₂Me | SO₂Me | H | Me | Me | — | |
| 1.122 | SO₂Me | SO₂Me | H | Me | Me | CH₂ | |
| 1.123 | SO₂Me | SO₂Me | H | Me | Et | — | |
| 1.124 | SO₂Me | SO₂Me | H | Me | Et | CH₂ | |
| 1.125 | SO₂Me | SO₂Me | H | Et | Me | — | |
| 1.126 | SO₂Me | SO₂Me | H | Et | Me | CH₂ | |
| 1.127 | SO₂Me | SO₂Me | H | Et | Et | — | |
| 1.128 | SO₂Me | SO₂Me | H | Et | Et | CH₂ | |
| 1.129 | Cl | SO₂Me | Me | Me | Me | —CH₂O— | d = 8.15 (d, J = 8.2 Hz, 1H), 7.76 (d, J = 8.1 Hz, 1H), 5.54 (s, 2H), 4.14 (s, 3H), 3.41 (s, 3H), 2.72 (s, 6H), 1.94 (s, 3H) |
| 1.130 | Cl | CF₃ | H | CF₃CH₂— | Me | — | δ = 11.21 (br s, 1H), 7.65-7.56 (m, 2H), 7.36 (br d, J = 7.9 Hz, 1H), 4.21 (q, J = 9.0 Hz, 0.9H), 4.12 (s, 3H), 3.84 (q, J = 8.4 Hz, 1.1H), 3.21 (s, 3H) |
| 1.131 | Cl | CF₃ | H | Me | -phenyl | — | 1H NMR (400 MHz, chloroform) δ = 10.63 (br s, 1H), 7.98 (s, 1H), 7.66 (d, J = 8.2 Hz, 1H), 7.46-7.34 (m, 3H), 7.24-7.16 (m, 3H), 4.11 (s, 3H), 3.56 (s, 3H) |
| 1.132 | Cl | CF₃ | H | —CH₂CH₂CH₂CH₂— | | — | δ = 10.46 (br s, 1H), 7.58 (d, J = 8.2 Hz, 1H), 7.49 (s, 1H), 7.30 (d, J = 7.8 Hz, 1H), 4.09 (s, 3H), 3.63 (br s, 2H), 3.53 (br t, J = 6.4 Hz, 2H), 2.11-1.94 (m, 4H) |
| 1.133 | Cl | CF₃ | Me | Me | Et | — | |
| 1.134 | Cl | CF₃ | H | —CH₂CH₂CH₂CH₂CH₂— | | — | δ = 10.52 (br s, 1H), 7.59 (d, J = 8.1 Hz, 1H), 7.35 (s, 1H), 7.30 (d, J = 7.9 Hz, 1H), 4.11 (s, 3H), 3.67 (br s, 2H), 3.34 (br s, 2H), 1.72 (br d, J = 4.5 Hz, 2H), 1.64 (br s, 4H) |
| 1.135 | Cl | CF₃ | H | —CH₂CH₂OCH₂CH₂— | | — | δ = 11.86 (br s, 1H), 7.71 (d, J = 8.1 Hz, 1H), 7.66 (s, 1H), 7.41 (d, J = 7.9 Hz, 1H), 4.00 (s, 3H), 3.63 (br s, 6H), 3.46 (br s, 2H) |
| 1.136 | Cl | CF₃ | H | Me | Et | — | δ = 10.46 (br s, 1H), 7.60 (d, J = 8.1 Hz, 1H), 7.40 (s, 0.6H), 7.35-7.28 (m, 1.4H), 4.11 (s, 3H), 3.56 (q, J = 6.8 Hz, 0.8H), 3.33 (q, J = 7.2 Hz, 1.2H), 3.08 (s, 1.8H), 3.04 (s, 1.2H), 1.24 (br t, J = 7.0 Hz, 3H) |

TABLE 1-continued

Examples of herbicidal compounds of the present invention.

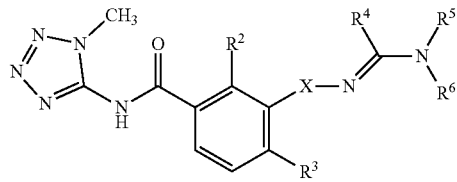

| Compound Number | R² | R³ | R⁴ | R⁵ | R⁶ | X | 1H-NMR (in CDCl₃ unless otherwise stated) |
|---|---|---|---|---|---|---|---|
| 1.137 | Cl | CF₃ | Me | Me | Me | —CH₂CH₂— | |
| 1.138 | Cl | CF₃ | Me | Me | Me | O | |
| 1.139 | Cl | CF₃ | CF₃ | Me | Me | — | 7.59 (d, 1H), 7.31 (d, J = 8.1 Hz, 1H), 4.11 (s, 3H), 3.17 (s, 6H) |
| 1.140 | Cl | CF₃ | H | Me | -iPr | — | 1HNMR (400 MHz, d4-methanol): 1.23-1.32 (m, 6H), 2.90-2.99 (m, 3H), 3.67-3.83 (m, 1H), 3.99-4.09 (m, 3H), 7.30-7.39 (m, 1H), 7.54 (s, 1H), 7.61-7.72 (m, 1H) |
| 1.141 | Cl | SO₂Me | H | —CH₂CH₂OCH₂CH₂— | | — | 1HNMR (400 MHz, d4-methanol): 3.26-3.28 (m, 3H), 3.46-3.53 (m, 2H), 3.71-3.80 (m, 6H), 4.06 (s, 3H), 7.39 (d, 1H), 7.55 (s, 1H), 7.98 (d, 1H) |
| 1.142 | Cl | SO₂Me | H | Me | —CH₂CF₃ | — | 1HNMR (400 MHz, chloroform): 8.04-8.00 (m, 1H), 7.63 (d, 1H), 7.44-7.39 (m, 1H), 4.23 (q, 1H), 4.13 (s, 3H), 3.86 (q, 1H), 3.29-3.17 (m, 6H) |
| 1.143 | Me | SO₂Me | H | Me | —CH₂CF₃ | — | 1HNMR (400 MHz, d4-methanol): 7.92 (d, 1H), 7.49 (s, 1H), 7.42 (d, 1H), 4.41-4.29 (m, 1H), 4.14-4.03 (m, 4H), 3.25-3.13 (m, 6H), 2.27 (s, 3H) |
| 1.144 | Me | SO₂Me | H | Me | -iPr | — | 1HNMR (400 MHz, chloroform): 7.89 (d, 1H), 7.43-7.31 (m, 1.8H), 7.24 (s, 0.2H), 4.80 (td, 0.2H), 4.10 (s, 3H), 3.64 (sepet, 0.8H), 3.25-3.17 (m, 3H), 2.98 (s, 2.3H), 2.90 (s, 0.7H), 2.31 (s, 3H), 1.28 (d, 6H) |
| 1.145 | Cl | SO₂Me | H | Me | -phenyl | — | 1HNMR (400 MHz, chloroform): 10.24 (brs, 1H), 7.97 (d, 1H), 7.84 (s, 1H), 7.43 (d, 1H), 7.39-7.33 (m, 2H), 7.25-7.13 (m, 3H), 4.11 (s, 3H), 3.56 (s, 3H), 3.23 (s, 3H), 2.36 (s, 3H) |
| 1.146 | Me | SO₂Me | H | —CH₂CH₂OCH₂CH₂— | | — | 1HNMR (400 MHz, d4-methanol): 7.90 (d, 1H), 7.43-7.32 (m, 2H), 4.05 (s, 3H), 3.75 (brs, 6H), 3.45 (brd, 2H), 3.21 (s, 3H), 2.28 (s, 3H) |
| 1.147 | Me | CF₃ | H | —CH₂CH₂OCH₂CH₂— | | — | 1HNMR (400 MHz, d4-methanol): 7.58 (d, 1H), 7.39-7.31 (m, 2H), 4.05 (s, 3H), 3.72 (brs, 8H), 2.27 (s, 3H) |
| 1.148 | Cl | CF₃ | Me | Me | Me | — | 1HNMR (400 MHz, d4-methanol) 7.67 (d, 1H), 7.31 (d, 1H), 4.06 (s, 3H), 3.11 (s, 6H), 1.81 (s, 3H) |
| 1.149 | Cl | CHF₂ | H | Me | Me | — | |
| 1.150 | Cl | CHF₂ | H | Me | Me | CH₂ | |
| 1.151 | Cl | CHF₂ | H | Me | Et | — | |
| 1.152 | Cl | CHF₂ | H | Me | Et | CH₂ | |
| 1.153 | Cl | CHF₂ | H | Et | Me | — | |
| 1.154 | Cl | CHF₂ | H | Et | Me | CH₂ | |
| 1.155 | Cl | CHF₂ | H | Et | Et | — | |
| 1.156 | Cl | CHF₂ | H | Et | Et | CH₂ | |

TABLE 2

Examples of herbicidal compounds of the present invention.

[Structure: 5-methyl-1,3,4-oxadiazol-2-yl attached via NH-C(=O) to a benzene ring bearing R² (ortho), R³ (para), and at the other ortho position a group -X-N=C(R⁴)-N(R⁵)(R⁶)]

| Compound Number | R² | R³ | R⁴ | R⁵ | R⁶ | X | ¹H-NMR (in CDCl₃ unless otherwise stated) |
|---|---|---|---|---|---|---|---|
| 2.001 | Me | Me | H | Me | Me | — | |
| 2.002 | Me | Me | H | Me | Me | CH₂ | |
| 2.003 | Me | Me | H | Me | Et | — | |
| 2.004 | Me | Me | H | Me | Et | CH₂ | |
| 2.005 | Me | Me | H | Et | Me | — | |
| 2.006 | Me | Me | H | Et | Me | CH₂ | |
| 2.007 | Me | Me | H | Et | Et | — | |
| 2.008 | Me | Me | H | Et | Et | CH₂ | |
| 2.009 | Me | Cl | H | Me | Me | — | |
| 2.010 | Me | Cl | H | Me | Me | CH₂ | |
| 2.011 | Me | Cl | H | Me | Et | — | |
| 2.012 | Me | Cl | H | Me | Et | CH₂ | |
| 2.013 | Me | Cl | H | Et | Me | — | |
| 2.014 | Me | Cl | H | Et | Me | CH₂ | |
| 2.015 | Me | Cl | H | Et | Et | — | |
| 2.016 | Me | Cl | H | Et | Et | CH₂ | |
| 2.017 | Me | CF₃ | H | Me | Me | — | ¹HNMR(400 MHz,d4-methanol)7.55(d,1H),7.29(d,1H),7.25(d,1H),3.04(s,6H),2.51(s,3H),2.23(s,3H) |
| 2.018 | Me | CF₃ | H | Me | Me | CH₂ | |
| 2.019 | Me | CF₃ | H | Me | Et | — | |
| 2.020 | Me | CF₃ | H | Me | Et | CH₂ | |
| 2.021 | Me | CF₃ | H | Et | Me | — | |
| 2.022 | Me | CF₃ | H | Et | Me | CH₂ | |
| 2.023 | Me | CF₃ | H | Et | Et | — | |
| 2.024 | Me | CF₃ | H | Et | Et | CH₂ | |
| 2.025 | Me | SO₂Me | H | Me | Me | — | (DMSO) δ = 8.14-7.15 (m, 3H), 3.29 (s, 3H), 3.23-3.05 (m, 6H), 2.49 (br s, 3H), 2.32-2.15 (m, 3H) |
| 2.026 | Me | SO₂Me | H | Me | Me | CH₂ | |
| 2.027 | Me | SO₂Me | H | Me | Et | — | δ = 10.88(brs,1H), 7.86(d,1H), 7.33(s,0.7H), 7.30(d,1H), 7.24(s,0.3H), 3.62-3.51(m,0.7H), 3.30(q,1.3H), 3.21(s,3H), 3.05(s,2H), 3.01(s,1H), 2.54(s,3H), 2.29(s,3H), 1.32-1.19(m,3H) |
| 2.028 | Me | SO₂Me | H | Me | Et | CH₂ | |
| 2.029 | Me | SO₂Me | H | Et | Me | — | |
| 2.030 | Me | SO₂Me | H | Et | Me | CH₂ | |
| 2.031 | Me | SO₂Me | H | Et | Et | — | δ = 7.91-7.82(m,1H), 7.31-7.27(m,2H), 3.55(q,2H), 3.28(q,2H), 3.20(s,3H), 2.54(s,3H), 2.29(s,3H), 1.26(td,6H) |
| 2.032 | Me | SO₂Me | H | Et | Et | CH₂ | |
| 2.033 | Cl | Me | H | Me | Me | — | |
| 2.034 | Cl | Me | H | Me | Me | CH₂ | |
| 2.035 | Cl | Me | H | Me | Et | — | |
| 2.036 | Cl | Me | H | Me | Et | CH₂ | |
| 2.037 | Cl | Me | H | Et | Me | — | |
| 2.038 | Cl | Me | H | Et | Me | CH₂ | |
| 2.039 | Cl | Me | H | Et | Et | — | |
| 2.040 | Cl | Me | H | Et | Et | CH₂ | |
| 2.041 | Cl | Cl | H | Me | Me | — | |
| 2.042 | Cl | Cl | H | Me | Me | CH₂ | |
| 2.043 | Cl | Cl | H | Me | Et | — | |
| 2.044 | Cl | Cl | H | Me | Et | CH₂ | |
| 2.045 | Cl | Cl | H | Et | Me | — | |
| 2.046 | Cl | Cl | H | Et | Me | CH₂ | |

TABLE 2-continued

Examples of herbicidal compounds of the present invention.

| Compound Number | R² | R³ | R⁴ | R⁵ | R⁶ | X | ¹H-NMR (in CDCl₃ unless otherwise stated) |
|---|---|---|---|---|---|---|---|
| 2.047 | Cl | Cl | H | Et | Et | — | |
| 2.048 | Cl | Cl | H | Et | Et | CH₂ | |
| 2.049 | Cl | CF₃ | H | Me | Me | — | (DMSO) δ = 7.60-7.50 (m, 2H), 7.18-7.11 (m, 1H), 3.02 (s, 3H), 2.98-2.90 (m, 3H), 2.46-2.33 (m, 3H) |
| 2.050 | Cl | CF₃ | H | Me | Me | CH₂ | |
| 2.051 | Cl | CF₃ | H | Me | Et | — | |
| 2.052 | Cl | CF₃ | H | Me | Et | CH₂ | |
| 2.053 | Cl | CF₃ | H | Et | Me | — | |
| 2.054 | Cl | CF₃ | H | Et | Me | CH₂ | |
| 2.055 | Cl | CF₃ | H | Et | Et | — | δ = 7.54 (d, J = 8.1 Hz, 1H), 7.29-7.26 (m, 2H), 3.52 (q, J = 7.1 Hz, 2H), 3.28 (q, J = 7.1 Hz, 2H), 2.54 (s, 3H), 1.28-1.21 (m, 6H) |
| 2.056 | Cl | CF₃ | H | Et | Et | CH₂ | |
| 2.057 | Cl | SO₂Me | H | Me | Me | — | δ = 7.95(d,1H), 7.51(s,1H), 7.28(d,1H), 3.30 (s, 3H), 3.10(s,6H), 2.51(s,3H) |
| 2.058 | Cl | SO₂Me | H | Me | Me | CH₂ | |
| 2.059 | Cl | SO₂Me | H | Me | Et | — | |
| 2.060 | Cl | SO₂Me | H | Me | Et | CH₂ | |
| 2.061 | Cl | SO₂Me | H | Et | Me | — | |
| 2.062 | Cl | SO₂Me | H | Et | Me | CH₂ | |
| 2.063 | Cl | SO₂Me | H | Et | Et | — | |
| 2.064 | Cl | SO₂Me | H | Et | Et | CH₂ | |
| 2.065 | CF₃ | Me | H | Me | Me | — | |
| 2.066 | CF₃ | Me | H | Me | Me | CH₂ | |
| 2.067 | CF₃ | Me | H | Me | Et | — | |
| 2.068 | CF₃ | Me | H | Me | Et | CH₂ | |
| 2.069 | CF₃ | Me | H | Et | Me | — | |
| 2.070 | CF₃ | Me | H | Et | Me | CH₂ | |
| 2.071 | CF₃ | Me | H | Et | Et | — | |
| 2.072 | CF₃ | Me | H | Et | Et | CH₂ | |
| 2.073 | CF₃ | Cl | H | Me | Me | — | |
| 2.074 | CF₃ | Cl | H | Me | Me | CH₂ | |
| 2.075 | CF₃ | Cl | H | Me | Et | — | |
| 2.076 | CF₃ | Cl | H | Me | Et | CH₂ | |
| 2.077 | CF₃ | Cl | H | Et | Me | — | |
| 2.078 | CF₃ | Cl | H | Et | Me | CH₂ | |
| 2.079 | CF₃ | Cl | H | Et | Et | — | |
| 2.080 | CF₃ | Cl | H | Et | Et | CH₂ | |
| 2.081 | CF₃ | CF₃ | H | Me | Me | — | |
| 2.082 | CF₃ | CF₃ | H | Me | Me | CH₂ | |
| 2.083 | CF₃ | CF₃ | H | Me | Et | — | |
| 2.084 | CF₃ | CF₃ | H | Me | Et | CH₂ | |
| 2.085 | CF₃ | CF₃ | H | Et | Me | — | |
| 2.086 | CF₃ | CF₃ | H | Et | Me | CH₂ | |
| 2.087 | CF₃ | CF₃ | H | Et | Et | — | |
| 2.088 | CF₃ | CF₃ | H | Et | Et | CH₂ | |
| 2.089 | CF₃ | SO₂Me | H | Me | Me | — | |
| 2.090 | CF₃ | SO₂Me | H | Me | Me | CH₂ | |
| 2.091 | CF₃ | SO₂Me | H | Me | Et | — | |
| 2.092 | CF₃ | SO₂Me | H | Me | Et | CH₂ | |
| 2.093 | CF₃ | SO₂Me | H | Et | Me | — | |
| 2.094 | CF₃ | SO₂Me | H | Et | Me | CH₂ | |
| 2.095 | CF₃ | SO₂Me | H | Et | Et | — | |
| 2.096 | CF₃ | SO₂Me | H | Et | Et | CH₂ | |
| 2.097 | SO₂Me | Me | H | Me | Me | — | |
| 2.098 | SO₂Me | Me | H | Me | Me | CH₂ | |

TABLE 2-continued

Examples of herbicidal compounds of the present invention.

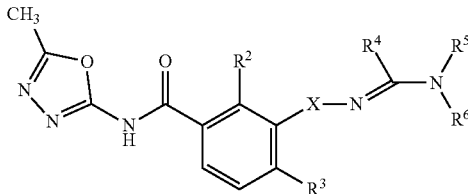

| Compound Number | R² | R³ | R⁴ | R⁵ | R⁶ | X | ¹H-NMR (in CDCl₃ unless otherwise stated) |
|---|---|---|---|---|---|---|---|
| 2.099 | SO₂Me | Me | H | Me | Et | — | |
| 2.100 | SO₂Me | Me | H | Me | Et | CH₂ | |
| 2.101 | SO₂Me | Me | H | Et | Me | — | |
| 2.102 | SO₂Me | Me | H | Et | Me | CH₂ | |
| 2.103 | SO₂Me | Me | H | Et | Et | — | |
| 2.104 | SO₂Me | Me | H | Et | Et | CH₂ | |
| 2.105 | SO₂Me | Cl | H | Me | Me | — | |
| 2.106 | SO₂Me | Cl | H | Me | Me | CH₂ | |
| 2.107 | SO₂Me | Cl | H | Me | Et | — | |
| 2.108 | SO₂Me | Cl | H | Me | Et | CH₂ | |
| 2.109 | SO₂Me | Cl | H | Et | Me | — | |
| 2.110 | SO₂Me | Cl | H | Et | Me | CH₂ | |
| 2.111 | SO₂Me | Cl | H | Et | Et | — | |
| 2.112 | SO₂Me | Cl | H | Et | Et | CH₂ | |
| 2.113 | SO₂Me | CF₃ | H | Me | Me | — | |
| 2.114 | SO₂Me | CF₃ | H | Me | Me | CH₂ | |
| 2.115 | SO₂Me | CF₃ | H | Me | Et | — | |
| 2.116 | SO₂Me | CF₃ | H | Me | Et | CH₂ | |
| 2.117 | SO₂Me | CF₃ | H | Et | Me | — | |
| 2.118 | SO₂Me | CF₃ | H | Et | Me | CH₂ | |
| 2.119 | SO₂Me | CF₃ | H | Et | Et | — | |
| 2.120 | SO₂Me | CF₃ | H | Et | Et | CH₂ | |
| 2.121 | SO₂Me | SO₂Me | H | Me | Me | — | |
| 2.122 | SO₂Me | SO₂Me | H | Me | Me | CH₂ | |
| 2.123 | SO₂Me | SO₂Me | H | Me | Et | — | |
| 2.124 | SO₂Me | SO₂Me | H | Me | Et | CH₂ | |
| 2.125 | SO₂Me | SO₂Me | H | Et | Me | — | |
| 2.126 | SO₂Me | SO₂Me | H | Et | Me | CH₂ | |
| 2.127 | SO₂Me | SO₂Me | H | Et | Et | — | |
| 2.128 | SO₂Me | SO₂Me | H | Et | Et | CH₂ | |
| 2.129 | Cl | SO₂Me | Me | Me | Me | —CH₂O— | δ = 8.13 (d, J = 8.2 Hz, 1H), 7.75 (d, J = 8.2 Hz, 1H), 5.55 (s, 2H), 3.40 (s, 3H), 2.73 (s, 6H), 2.54 (s, 3H), 1.94 (s, 3H) |
| 2.130 | Cl | CF₃ | H | CF₃CH₂— | Me | — | δ = 7.54 (m, 1H), 7.40 (m, 1H), 7.31 (m, 1H), 4.19 (q, J = 9.0 Hz, 0.9H), 3.78 (q, J = 8.4 Hz, 1.1H), 3.19 (s, 1.8H), 3.16 (s, 1.2H), 2.52 (s, 3H) |
| 2.131 | Cl | CF₃ | H | Me | —phenyl | — | δ = 11.12 (br s, 1H), 7.97 (s, 1H), 7.60 (d, J = 8.1 Hz, 1H), 7.41-7.36 (m, 2H), 7.33 (d, J = 7.9 Hz, 1H), 7.22-7.13 (m, 3H), 3.54 (s, 3H), 2.38 (s, 3H) |
| 2.132 | Cl | CF₃ | H | —CH₂CH₂CH₂CH₂— | | — | δ = 7.60-7.50 (m, 2H), 7.28 (d, J = 8.6 Hz, 1H), 3.60-3.49 (m, 4H), 2.54 (s, 3H), 2.05-1.94 (m, 4H) |

TABLE 2-continued

Examples of herbicidal compounds of the present invention.

| Compound Number | R² | R³ | R⁴ | R⁵ | R⁶ | X | ¹H-NMR (in CDCl₃ unless otherwise stated) |
|---|---|---|---|---|---|---|---|
| 2.133 | Cl | CF₃ | Me | Me | Et | — | |
| 2.134 | Cl | CF₃ | H | —CH₂CH₂CH₂CH₂CH₂— | — | | |
| 2.135 | Cl | CF₃ | H | —CH₂CH₂OCH₂CH₂— | — | | |
| 2.136 | Cl | CF₃ | H | Me | Et | — | δ = 10.15 (br s, 1H), 7.55 (d, J = 8.2 Hz, 1H), 7.35 (s, 0.6H), 7.29 (d, J = 8.2 Hz, 1H), 7.26 (s, 0.4H), 3.54 (q, J = 6.9 Hz, 0.8H), 3.31 (q, J = 7.2 Hz, 1.2H), 3.04 (s, 1.8H), 3.01 (s, 1.2H), 2.54 (s, 3H), 1.26-1.20 (m, 3H) |
| 2.137 | Cl | CF₃ | Me | Me | Me | —CH₂CH₂— | |
| 2.138 | Cl | CF₃ | Me | Me | Me | O | |
| 2.139 | Cl | CF₃ | CF₃ | Me | Me | — | |
| 2.140 | Cl | CF₃ | H | Me | —iPr | — | 1HNMR(400 MHz,d4-methanol)1.18-1.34(m,6H), 2.45-2.54(m,3H), 2.90-3.00(m,3H), 3.68-3.80(m,1H), 7.21-7.31(m,1H), 7.36(d,1H), 7.53(s,1H), 7.58-7.70(m,1H) |
| 2.141 | Cl | SO₂Me | H | —CH₂CH₂OCH₂CH₂— | — | | |
| 2.142 | Cl | SO₂Me | H | Me | —CH₂CF₃ | — | δ = 8.01-7.96(m,1H), 7.56-7.40(m,2H), 4.27-4.17(m,1H), 3.81(q, 1H), 3.26-3.14(m,6H), 2.55(s,3H) |
| 2.143 | Me | SO₂Me | H | Me | —CH₂CF₃ | — | 1HNMR(400 MHz,d4-methanol): 7.89(d,1H), 7.48(s,1H), 7.31(d,1H), 4.34(q,0.7H), 4.08(q,1.3H), 3.26-3.10(m,6H), 2.51(s,3H), 2.23(s,3H) |
| 2.144 | Me | SO₂Me | H | Me | —iPr | — | 1H NMR(400MHz,d4-methanol): 7.87(d,1H), 7.43(s,0.8H), 7.27(d,1.2H), 3.72(td,1H), 3.22(s,3H), 3.00(s,2.4H), 2.92(s,0.6H), 2.51(s,3H), 2.24(s,3H), 1.28(d,6H) |
| 2.145 | Cl | SO₂Me | H | Me | —phenyl | — | δ = 7.96(d,1H), 7.87(s,1H), 7.41-7.34(m,3H), 7.25-7.14(m,3H), 3.56(s,3H), 3.23(s,3H), 2.43(s,3H), 2.35(s,3H) |
| 2.146 | Me | SO₂Me | H | —CH₂CH₂OCH₂CH₂— | — | | 1HNMR(400 MHz,d4-methanol): 7.87(d,1H), 7.36(s,1H), 7.28(d,1H), 3.75(brs,6H), 3.54-3.37(m,2H), 3.20(s,3H), 2.51(s,3H), 2.24(s,3H) |
| 2.147 | Me | CF₃ | H | —CH₂CH₂OCH₂CH₂— | — | | 1HNMR(400 MHz,d4-methanol): 7.55(d,1H), 7.34(d,1H), 7.25(d,1H), 3.81-3.36(m,8H), 2.51(s,3H), 2.23(s,3H) |

TABLE 2-continued

Examples of herbicidal compounds of the present invention.

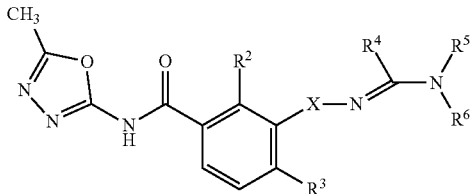

| Compound Number | R² | R³ | R⁴ | R⁵ | R⁶ | X | ¹H-NMR (in CDCl₃ unless otherwise stated) |
|---|---|---|---|---|---|---|---|
| 2.148 | Cl | CF₃ | Me | Me | Me | — | 1HNMR(400 MHz,d4-methanol)7.64(d,1H),7.23(d,1H),3.10(s,6H),2.50(s,3H),1.80(s,3H) |
| 2.149 | Cl | CHF₂ | H | Me | Me | — | |
| 2.150 | Cl | CHF₂ | H | Me | Me | CH₂ | |
| 2.151 | Cl | CHF₂ | H | Me | Et | — | |
| 2.152 | Cl | CHF₂ | H | Me | Et | CH₂ | |
| 2.153 | Cl | CHF₂ | H | Et | Me | — | |
| 2.154 | Cl | CHF₂ | H | Et | Me | CH₂ | |
| 2.155 | Cl | CHF₂ | H | Et | Et | — | |
| 2.156 | Cl | CHF₂ | H | Et | Et | CH₂ | |

TABLE 3

Examples of herbicidal compounds of the present invention.

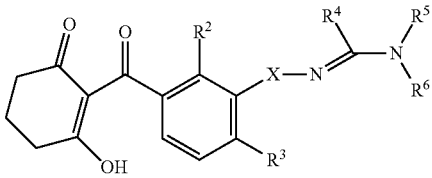

| Compound Number | R² | R³ | R⁴ | R⁵ | R⁶ | X | 1H-NMR (in CDCl₃ unless otherwise stated) |
|---|---|---|---|---|---|---|---|
| 3.001 | Me | Me | H | Me | Me | — | |
| 3.002 | Me | Me | H | Me | Me | CH₂ | |
| 3.003 | Me | Me | H | Me | Et | — | |
| 3.004 | Me | Me | H | Me | Et | CH₂ | |
| 3.005 | Me | Me | H | Et | Me | — | |
| 3.006 | Me | Me | H | Et | Me | CH₂ | |
| 3.007 | Me | Me | H | Et | Et | — | |
| 3.008 | Me | Me | H | Et | Et | CH₂ | |
| 3.009 | Me | Cl | H | Me | Me | — | |
| 3.010 | Me | Cl | H | Me | Me | CH₂ | |
| 3.011 | Me | Cl | H | Me | Et | — | |
| 3.012 | Me | Cl | H | Me | Et | CH₂ | |
| 3.013 | Me | Cl | H | Et | Me | — | |
| 3.014 | Me | Cl | H | Et | Me | CH₂ | |
| 3.015 | Me | Cl | H | Et | Et | — | |
| 3.016 | Me | Cl | H | Et | Et | CH₂ | |
| 3.017 | Me | CF₃ | H | Me | Me | — | 1HNMR(400 MHz,d4-methanol) 7.75(brs,1H),7.51(d,1H),7.05(d,1H), 3.18(brd,6H),2.49(t,4H),2.11(s,3H),1.97(quin, 2H) |
| 3.018 | Me | CF₃ | H | Me | Me | CH₂ | |
| 3.019 | Me | CF₃ | H | Me | Et | — | |
| 3.020 | Me | CF₃ | H | Me | Et | CH₂ | |
| 3.021 | Me | CF₃ | H | Et | Me | — | |
| 3.022 | Me | CF₃ | H | Et | Me | CH₂ | |
| 3.023 | Me | CF₃ | H | Et | Et | — | |
| 3.024 | Me | CF₃ | H | Et | Et | CH₂ | |

TABLE 3-continued

Examples of herbicidal compounds of the present invention.

| Compound Number | R² | R³ | R⁴ | R⁵ | R⁶ | X | 1H-NMR (in CDCl₃ unless otherwise stated) |
|---|---|---|---|---|---|---|---|
| 3.025 | Me | SO₂Me | H | Me | Me | — | (DMSO) δ = 7.66 (d, J = 8.1 Hz, 1H), 7.40 (s, 1H), 6.90 (d, J = 8.2 Hz, 1H), 3.24 (s, 3H), 3.00 (br d, J = 4.6 Hz, 6H), 2.64-2.51 (m, 4H), 1.99-1.91 (m, 5H) |
| 3.026 | Me | SO₂Me | H | Me | Me | CH₂ | |
| 3.027 | Me | SO₂Me | H | Me | Et | — | |
| 3.028 | Me | SO₂Me | H | Me | Et | CH₂ | |
| 3.029 | Me | SO₂Me | H | Et | Me | — | |
| 3.030 | Me | SO₂Me | H | Et | Me | CH₂ | |
| 3.031 | Me | SO₂Me | H | Et | Et | — | |
| 3.032 | Me | SO₂Me | H | Et | Et | CH₂ | |
| 3.033 | Cl | Me | H | Me | Me | — | |
| 3.034 | Cl | Me | H | Me | Me | CH₂ | |
| 3.035 | Cl | Me | H | Me | Et | — | |
| 3.036 | Cl | Me | H | Me | Et | CH₂ | |
| 3.037 | Cl | Me | H | Et | Me | — | |
| 3.038 | Cl | Me | H | Et | Me | CH₂ | |
| 3.039 | Cl | Me | H | Et | Et | — | |
| 3.040 | Cl | Me | H | Et | Et | CH₂ | |
| 3.041 | Cl | Cl | H | Me | Me | — | |
| 3.042 | Cl | Cl | H | Me | Me | CH₂ | |
| 3.043 | Cl | Cl | H | Me | Et | — | |
| 3.044 | Cl | Cl | H | Me | Et | CH₂ | |
| 3.045 | Cl | Cl | H | Et | Me | — | |
| 3.046 | Cl | Cl | H | Et | Me | CH₂ | |
| 3.047 | Cl | Cl | H | Et | Et | — | |
| 3.048 | Cl | Cl | H | Et | Et | CH₂ | |
| 3.049 | Cl | CF₃ | H | Me | Me | — | (DMSO): 7.59-7.49 (m, 2H), 6.94 (d, J = 8.1 Hz, 1H), 3.01 (s, 3H), 2.97-2.90 (m, 3H), 2.70-2.51 (m, 4H), 1.93 (quin, J = 6.3 Hz, 2H) |
| 3.050 | Cl | CF₃ | H | Me | Me | CH₂ | |
| 3.051 | Cl | CF₃ | H | Me | Et | — | |
| 3.052 | Cl | CF₃ | H | Me | Et | CH₂ | |
| 3.053 | Cl | CF₃ | H | Et | Me | — | |
| 3.054 | Cl | CF₃ | H | Et | Me | CH₂ | |
| 3.055 | Cl | CF₃ | H | Et | Et | — | |
| 3.056 | Cl | CF₃ | H | Et | Et | CH₂ | |
| 3.057 | Cl | SO₂Me | H | Me | Me | — | 1HNMR(400 MHz,chloroform): 7.95(d,1H), 7.42(s,1H), 6.87(d,1H), 3.29(s,3H), 3.06(d,6H), 2.80(t,2H), 2.45(t, 2H), 2.06(quin,2H) |
| 3.058 | Cl | SO₂Me | H | Me | Me | CH₂ | |
| 3.059 | Cl | SO₂Me | H | Me | Et | — | |
| 3.060 | Cl | SO₂Me | H | Me | Et | CH₂ | |
| 3.061 | Cl | SO₂Me | H | Et | Me | — | |
| 3.062 | Cl | SO₂Me | H | Et | Me | CH₂ | |
| 3.063 | Cl | SO₂Me | H | Et | Et | — | |
| 3.064 | Cl | SO₂Me | H | Et | Et | CH₂ | |
| 3.065 | CF₃ | Me | H | Me | Me | — | |
| 3.066 | CF₃ | Me | H | Me | Me | CH₂ | |
| 3.067 | CF₃ | Me | H | Me | Et | — | |
| 3.068 | CF₃ | Me | H | Me | Et | CH₂ | |
| 3.069 | CF₃ | Me | H | Et | Me | — | |
| 3.070 | CF₃ | Me | H | Et | Me | CH₂ | |
| 3.071 | CF₃ | Me | H | Et | Et | — | |
| 3.072 | CF₃ | Me | H | Et | Et | CH₂ | |
| 3.073 | CF₃ | Cl | H | Me | Me | — | |
| 3.074 | CF₃ | Cl | H | Me | Me | CH₂ | |
| 3.075 | CF₃ | Cl | H | Me | Et | — | |
| 3.076 | CF₃ | Cl | H | Me | Et | CH₂ | |
| 3.077 | CF₃ | Cl | H | Et | Me | — | |
| 3.078 | CF₃ | Cl | H | Et | Me | CH₂ | |

TABLE 3-continued

Examples of herbicidal compounds of the present invention.

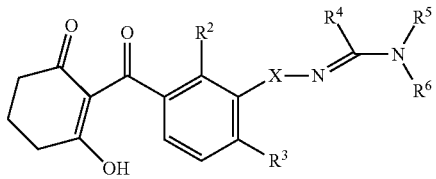

| Compound Number | $R^2$ | $R^3$ | $R^4$ | $R^5$ | $R^6$ | X | 1H-NMR (in $CDCl_3$ unless otherwise stated) |
|---|---|---|---|---|---|---|---|
| 3.079 | $CF_3$ | Cl | H | Et | Et | — | |
| 3.080 | $CF_3$ | Cl | H | Et | Et | $CH_2$ | |
| 3.081 | $CF_3$ | $CF_3$ | H | Me | Me | — | |
| 3.082 | $CF_3$ | $CF_3$ | H | Me | Me | $CH_2$ | |
| 3.083 | $CF_3$ | $CF_3$ | H | Me | Et | — | |
| 3.084 | $CF_3$ | $CF_3$ | H | Me | Et | $CH_2$ | |
| 3.085 | $CF_3$ | $CF_3$ | H | Et | Me | — | |
| 3.086 | $CF_3$ | $CF_3$ | H | Et | Me | $CH_2$ | |
| 3.087 | $CF_3$ | $CF_3$ | H | Et | Et | — | |
| 3.088 | $CF_3$ | $CF_3$ | H | Et | Et | $CH_2$ | |
| 3.089 | $CF_3$ | $SO_2Me$ | H | Me | Me | — | |
| 3.090 | $CF_3$ | $SO_2Me$ | H | Me | Me | $CH_2$ | |
| 3.091 | $CF_3$ | $SO_2Me$ | H | Me | Et | — | |
| 3.092 | $CF_3$ | $SO_2Me$ | H | Me | Et | $CH_2$ | |
| 3.093 | $CF_3$ | $SO_2Me$ | H | Et | Me | — | |
| 3.094 | $CF_3$ | $SO_2Me$ | H | Et | Me | $CH_2$ | |
| 3.095 | $CF_3$ | $SO_2Me$ | H | Et | Et | — | |
| 3.096 | $CF_3$ | $SO_2Me$ | H | Et | Et | $CH_2$ | |
| 3.097 | $SO_2Me$ | Me | H | Me | Me | — | |
| 3.098 | $SO_2Me$ | Me | H | Me | Me | $CH_2$ | |
| 3.099 | $SO_2Me$ | Me | H | Me | Et | — | |
| 3.100 | $SO_2Me$ | Me | H | Me | Et | $CH_2$ | |
| 3.101 | $SO_2Me$ | Me | H | Et | Me | — | |
| 3.102 | $SO_2Me$ | Me | H | Et | Me | $CH_2$ | |
| 3.103 | $SO_2Me$ | Me | H | Et | Et | — | |
| 3.104 | $SO_2Me$ | Me | H | Et | Et | $CH_2$ | |
| 3.105 | $SO_2Me$ | Cl | H | Me | Me | — | |
| 3.106 | $SO_2Me$ | Cl | H | Me | Me | $CH_2$ | |
| 3.107 | $SO_2Me$ | Cl | H | Me | Et | — | |
| 3.108 | $SO_2Me$ | Cl | H | Me | Et | $CH_2$ | |
| 3.109 | $SO_2Me$ | Cl | H | Et | Me | — | |
| 3.110 | $SO_2Me$ | Cl | H | Et | Me | $CH_2$ | |
| 3.111 | $SO_2Me$ | Cl | H | Et | Et | — | |
| 3.112 | $SO_2Me$ | Cl | H | Et | Et | $CH_2$ | |
| 3.113 | $SO_2Me$ | $CF_3$ | H | Me | Me | — | |
| 3.114 | $SO_2Me$ | $CF_3$ | H | Me | Me | $CH_2$ | |
| 3.115 | $SO_2Me$ | $CF_3$ | H | Me | Et | — | |
| 3.116 | $SO_2Me$ | $CF_3$ | H | Me | Et | $CH_2$ | |
| 3.117 | $SO_2Me$ | $CF_3$ | H | Et | Me | — | |
| 3.118 | $SO_2Me$ | $CF_3$ | H | Et | Me | $CH_2$ | |
| 3.119 | $SO_2Me$ | $CF_3$ | H | Et | Et | — | |
| 3.120 | $SO_2Me$ | $CF_3$ | H | Et | Et | $CH_2$ | |
| 3.121 | $SO_2Me$ | $SO_2Me$ | H | Me | Me | — | |
| 3.122 | $SO_2Me$ | $SO_2Me$ | H | Me | Me | $CH_2$ | |
| 3.123 | $SO_2Me$ | $SO_2Me$ | H | Me | Et | — | |
| 3.124 | $SO_2Me$ | $SO_2Me$ | H | Me | Et | $CH_2$ | |
| 3.125 | $SO_2Me$ | $SO_2Me$ | H | Et | Me | — | |
| 3.126 | $SO_2Me$ | $SO_2Me$ | H | Et | Me | $CH_2$ | |
| 3.127 | $SO_2Me$ | $SO_2Me$ | H | Et | Et | — | |
| 3.128 | $SO_2Me$ | $SO_2Me$ | H | Et | Et | $CH_2$ | |

TABLE 3-continued

Examples of herbicidal compounds of the present invention.

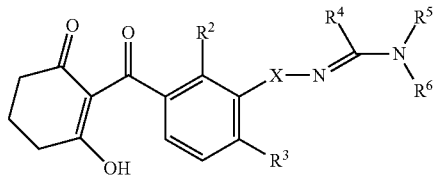

| Compound Number | R² | R³ | R⁴ | R⁵ | R⁶ | X | 1H-NMR (in CDCl₃ unless otherwise stated) |
|---|---|---|---|---|---|---|---|
| 3.129 | Cl | SO₂Me | Me | Me | Me | —CH₂O— | δ = 8.12 (d, J = 8.1 Hz, 1H), 5.54 (s, 2H), 3.37 (s, 3H), 2.81 (t, J = 6.4 Hz, 2H), 2.73 (s, 6H), 2.44 (t, J = 6.4 Hz, 2H), 2.13-2.02 (m, 2H), 1.92 (s, 3H) |
| 3.130 | Cl | CF₃ | H | CF₃CH₂— | Me | — | 1H NMR(400 MHz,d4-methanol): 7.69-7.54(m,2H), 7.06-6.93(m,1H), 4.27(q, 0.6H), 4.11(q, 1.4H), 3.17(s,3H), 2.87-2.40(m,4H), 2.04(quin,2H) |
| 3.131 | Cl | CF₃ | H | Me | —phenyl | — | |
| 3.132 | Cl | CF₃ | H | —CH₂CH₂CH₂CH₂— | | — | |
| 3.133 | Cl | CF₃ | Me | Me | Et | — | |
| 3.134 | Cl | CF₃ | H | —CH₂CH₂CH₂CH₂CH₂— | | — | |
| 3.135 | Cl | CF₃ | H | —CH₂CH₂OCH₂CH₂— | | — | |
| 3.136 | Cl | CF₃ | H | Me | Et | — | |
| 3.137 | Cl | CF₃ | Me | Me | Me | —CH₂CH₂— | |
| 3.138 | Cl | CF₃ | Me | Me | Me | O | |
| 3.139 | Cl | CF₃ | CF₃ | Me | Me | — | |
| 3.140 | Cl | CF₃ | H | Me | —iPr | — | |
| 3.141 | Cl | SO₂Me | H | —CH₂CH₂OCH₂CH₂— | | — | |
| 3.142 | Cl | SO₂Me | H | Me | —CH₂CF₃ | — | |
| 3.143 | Me | SO₂Me | H | Me | —CH₂CF₃ | — | |
| 3.144 | Me | SO₂Me | H | Me | —iPr | — | |
| 3.145 | Cl | SO₂Me | H | Me | —phenyl | — | |
| 3.146 | Me | SO₂Me | H | —CH₂CH₂OCH₂CH₂— | | — | |
| 3.147 | Me | CF₃ | H | —CH₂CH₂OCH₂CH₂— | | — | |
| 3.148 | Cl | CF₃ | Me | Me | Me | — | |
| 3.149 | Cl | CHF₂ | H | Me | Me | — | |
| 3.150 | Cl | CHF₂ | H | Me | Me | CH₂ | |
| 3.151 | Cl | CHF₂ | H | Me | Et | — | |
| 3.152 | Cl | CHF₂ | H | Me | Et | CH₂ | |
| 3.153 | Cl | CHF₂ | H | Et | Me | — | |
| 3.154 | Cl | CHF₂ | H | Et | Me | CH₂ | |
| 3.155 | Cl | CHF₂ | H | Et | Et | — | |
| 3.156 | Cl | CHF₂ | H | Et | Et | CH₂ | |

TABLE 4

Examples of herbicidal compounds of the present invention.

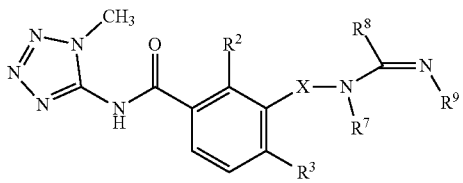

| Compound Number | R² | R³ | R⁷ | R⁸ | R⁹ | X | 1H-NMR (in CDCl₃ unless otherwise stated) |
|---|---|---|---|---|---|---|---|
| 4.001 | Me | Me | Me | Me | MeO | — | |
| 4.002 | Me | Me | Me | Me | MeO | CH₂ | |
| 4.003 | Me | Cl | Me | Me | MeO | — | |
| 4.004 | Me | Cl | Me | Me | MeO | CH₂ | |
| 4.005 | Me | CF₃ | Me | Me | MeO | — | |
| 4.006 | Me | CF₃ | Me | Me | MeO | CH₂ | |
| 4.007 | Me | SO₂Me | Me | Me | MeO | — | |
| 4.008 | Me | SO₂Me | Me | Me | MeO | CH₂ | |
| 4.009 | Cl | Me | Me | Me | MeO | — | |

TABLE 4-continued

Examples of herbicidal compounds of the present invention.

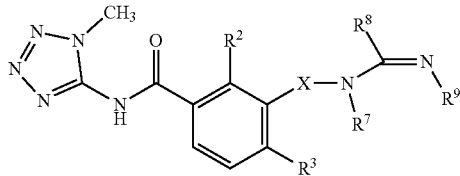

| Compound Number | R² | R³ | R⁷ | R⁸ | R⁹ | X | 1H-NMR (in CDCl₃ unless otherwise stated) |
|---|---|---|---|---|---|---|---|
| 4.010 | Cl | Me | Me | Me | MeO | CH₂ | |
| 4.011 | Cl | Cl | Me | Me | MeO | — | |
| 4.012 | Cl | Cl | Me | Me | MeO | CH₂ | |
| 4.013 | Cl | CF₃ | Me | Me | MeO | — | |
| 4.014 | Cl | CF₃ | Me | Me | MeO | CH₂ | (Methanol) δ = 7.94-7.84 (m, 1H), 7.79 (d, J = 8.1 Hz, 1H), 4.67 (s, 2H), 4.08 (s, 3H), 3.68 (s, 3H), 2.51 (s, 3H), 2.05 (s, 3H) |
| 4.015 | Cl | SO₂Me | Me | Me | MeO | — | |
| 4.016 | Cl | SO₂Me | Me | Me | MeO | CH₂ | (Methanol) δ = 8.20 (d, J = 8.2 Hz, 1H), 7.83 (d, J = 8.1 Hz, 1H), 4.95 (s, 2H), 4.06 (s, 3H), 3.68 (s, 3H), 3.27 (s, 3H), 2.60 (s, 3H), 2.06 (s, 3H) |
| 4.017 | CF₃ | Me | Me | Me | MeO | — | |
| 4.018 | CF₃ | Me | Me | Me | MeO | CH₂ | |
| 4.019 | CF₃ | Cl | Me | Me | MeO | — | |
| 4.020 | CF₃ | Cl | Me | Me | MeO | CH₂ | |
| 4.021 | CF₃ | CF₃ | Me | Me | MeO | — | |
| 4.022 | CF₃ | CF₃ | Me | Me | MeO | CH₂ | |
| 4.023 | CF₃ | SO₂Me | Me | Me | MeO | — | |
| 4.024 | CF₃ | SO₂Me | Me | Me | MeO | CH₂ | |
| 4.025 | SO₂Me | Me | Me | Me | MeO | — | |
| 4.026 | SO₂Me | Me | Me | Me | MeO | CH₂ | |
| 4.027 | SO₂Me | Cl | Me | Me | MeO | — | |
| 4.028 | SO₂Me | Cl | Me | Me | MeO | CH₂ | |
| 4.029 | SO₂Me | CF₃ | Me | Me | MeO | — | |
| 4.030 | SO₂Me | CF₃ | Me | Me | MeO | CH₂ | |
| 4.031 | SO₂Me | SO₂Me | Me | Me | MeO | — | |
| 4.032 | SO₂Me | SO₂Me | Me | Me | MeO | CH₂ | |
| 4.033 | Cl | SO₂Me | Me | Me | CN | CH₂ | 1H NMR (400 MHz, Methanol) d = 8.29-8.22 (m, 1H), 7.99-7.88 (m, 1H), 5.37 (s, 2H), 4.06 (s, 3H), 3.93 (s, 1H), 2.95 (s, 2H), 2.83-2.78 (m, 1H), 2.68-2.65 (m, 1H), 2.47 (s, 2H). |
| 4.034 | Cl | CF₃ | Me | Me | CN | CH₂ | 1H NMR (400 MHz, Methanol) d = 7.90 (d, J = 8.1 Hz, 1H), 7.83 (s, 1H), 5.09 (s, 2H), 4.06-3.95 (m, 3H), 2.84 (s, 2.25H), 2.74 (s, 0.75H), 2.64 (s, 0.75H), 2.47 (s, 2.25H) |

TABLE 5

Examples of herbicidal compounds of the present invention.

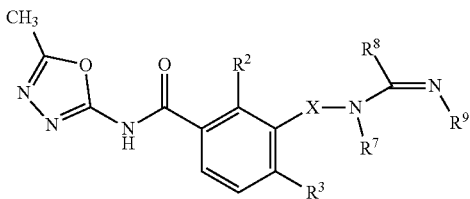

| Compound Number | $R^2$ | $R^3$ | $R^7$ | $R^8$ | $R^9$ | X | 1H-NMR (in $CDCl_3$ unless otherwise stated) |
|---|---|---|---|---|---|---|---|
| 5.001 | Me | Me | Me | Me | MeO | — | |
| 5.002 | Me | Me | Me | Me | MeO | $CH_2$ | |
| 5.003 | Me | Cl | Me | Me | MeO | — | |
| 5.004 | Me | Cl | Me | Me | MeO | $CH_2$ | |
| 5.005 | Me | $CF_3$ | Me | Me | MeO | — | |
| 5.006 | Me | $CF_3$ | Me | Me | MeO | $CH_2$ | |
| 5.007 | Me | $SO_2Me$ | Me | Me | MeO | — | |
| 5.008 | Me | $SO_2Me$ | Me | Me | MeO | $CH_2$ | |
| 5.009 | Cl | Me | Me | Me | MeO | — | |
| 5.010 | Cl | Me | Me | Me | MeO | $CH_2$ | |
| 5.011 | Cl | Cl | Me | Me | MeO | — | |
| 5.012 | Cl | Cl | Me | Me | MeO | $CH_2$ | |
| 5.013 | Cl | $CF_3$ | Me | Me | MeO | — | |
| 5.014 | Cl | $CF_3$ | Me | Me | MeO | $CH_2$ | (Methanol) δ = 7.83 (d, J = 8.1 Hz, 1H), 7.68 (d, J = 8.1 Hz, 1H), 4.65 (s, 2H), 3.68 (s, 3H), 2.55-2.44 (m, 6H), 2.04 (s, 3H) |
| 5.015 | Cl | $SO_2Me$ | Me | Me | MeO | — | |
| 5.016 | Cl | $SO_2Me$ | Me | Me | MeO | $CH_2$ | (Methanol) δ = 8.18 (d, J = 8.2 Hz, 1H), 7.75 (d, J = 8.2 Hz, 1H), 4.94 (s, 2H), 3.67 (s, 3H), 3.27 (s, 3H), 2.59 (s, 3H), 2.51 (s, 3H), 2.06 (s, 3H) |
| 5.017 | $CF_3$ | Me | Me | Me | MeO | — | |
| 5.018 | $CF_3$ | Me | Me | Me | MeO | $CH_2$ | |
| 5.019 | $CF_3$ | Cl | Me | Me | MeO | — | |
| 5.020 | $CF_3$ | Cl | Me | Me | MeO | $CH_2$ | |
| 5.021 | $CF_3$ | $CF_3$ | Me | Me | MeO | — | |
| 5.022 | $CF_3$ | $CF_3$ | Me | Me | MeO | $CH_2$ | |
| 5.023 | $CF_3$ | $SO_2Me$ | Me | Me | MeO | — | |
| 5.024 | $CF_3$ | $SO_2Me$ | Me | Me | MeO | $CH_2$ | |
| 5.025 | $SO_2Me$ | Me | Me | Me | MeO | — | |
| 5.026 | $SO_2Me$ | Me | Me | Me | MeO | $CH_2$ | |
| 5.027 | $SO_2Me$ | Cl | Me | Me | MeO | — | |
| 5.028 | $SO_2Me$ | Cl | Me | Me | MeO | $CH_2$ | |
| 5.029 | $SO_2Me$ | $CF_3$ | Me | Me | MeO | — | |
| 5.030 | $SO_2Me$ | $CF_3$ | Me | Me | MeO | $CH_2$ | |
| 5.031 | $SO_2Me$ | $SO_2Me$ | Me | Me | MeO | — | |
| 5.032 | $SO_2Me$ | $SO_2Me$ | Me | Me | MeO | $CH_2$ | |
| 5.033 | Cl | $SO_2Me$ | Me | Me | CN | $CH_2$ | |
| 5.034 | Cl | $CF_3$ | Me | Me | CN | $CH_2$ | |

TABLE 6

Examples of herbicidal compounds of the present invention.

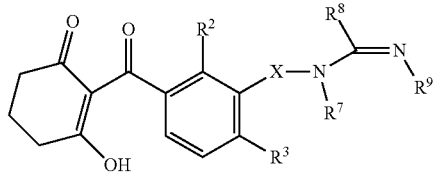

| Compound Number | R² | R³ | R⁷ | R⁸ | R⁹ | X | 1H-NMR (in CDCl₃ unless otherwise stated) |
|---|---|---|---|---|---|---|---|
| 6.001 | Me | Me | Me | Me | MeO | — | |
| 6.002 | Me | Me | Me | Me | MeO | CH₂ | |
| 6.003 | Me | Cl | Me | Me | MeO | — | |
| 6.004 | Me | Cl | Me | Me | MeO | CH₂ | |
| 6.005 | Me | CF₃ | Me | Me | MeO | — | |
| 6.006 | Me | CF₃ | Me | Me | MeO | CH₂ | |
| 6.007 | Me | SO₂Me | Me | Me | MeO | — | |
| 6.008 | Me | SO₂Me | Me | Me | MeO | CH₂ | |
| 6.009 | Cl | Me | Me | Me | MeO | — | |
| 6.010 | Cl | Me | Me | Me | MeO | CH₂ | |
| 6.011 | Cl | Cl | Me | Me | MeO | — | |
| 6.012 | Cl | Cl | Me | Me | MeO | CH₂ | |
| 6.013 | Cl | CF₃ | Me | Me | MeO | — | |
| 6.014 | Cl | CF₃ | Me | Me | MeO | CH₂ | |
| 6.015 | Cl | SO₂Me | Me | Me | MeO | — | |
| 6.016 | Cl | SO₂Me | Me | Me | MeO | CH₂ | |
| 6.017 | CF₃ | Me | Me | Me | MeO | — | |
| 6.018 | CF₃ | Me | Me | Me | MeO | CH₂ | |
| 6.019 | CF₃ | Cl | Me | Me | MeO | — | |
| 6.020 | CF₃ | Cl | Me | Me | MeO | CH₂ | |
| 6.021 | CF₃ | CF₃ | Me | Me | MeO | — | |
| 6.022 | CF₃ | CF₃ | Me | Me | MeO | CH₂ | |
| 6.023 | CF₃ | SO₂Me | Me | Me | MeO | — | |
| 6.024 | CF₃ | SO₂Me | Me | Me | MeO | CH₂ | |
| 6.025 | SO₂Me | Me | Me | Me | MeO | — | |
| 6.026 | SO₂Me | Me | Me | Me | MeO | CH₂ | |
| 6.027 | SO₂Me | Cl | Me | Me | MeO | — | |
| 6.028 | SO₂Me | Cl | Me | Me | MeO | CH₂ | |
| 6.029 | SO₂Me | CF₃ | Me | Me | MeO | — | |
| 6.030 | SO₂Me | CF₃ | Me | Me | MeO | CH₂ | |
| 6.031 | SO₂Me | SO₂Me | Me | Me | MeO | — | |
| 6.032 | SO₂Me | SO₂Me | Me | Me | MeO | CH₂ | |
| 6.033 | Cl | SO₂Me | Me | Me | CN | CH₂ | |
| 6.034 | Cl | CF₃ | Me | Me | CN | CH₂ | |

TABLE 7

Examples of herbicidal compounds of the present invention.

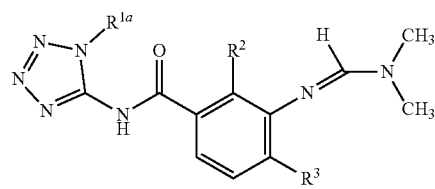

| Compound Number | R¹ᵃ | R² | R³ | 1H-NMR (in CDCl₃ unless otherwise stated) |
|---|---|---|---|---|
| 7.001 | Et | Me | SO₂Me | 7.95 (d, 1H), 7.33 (d, 1H), 7.27 (s, 1H), 4.47 (q, J = 7.3 Hz, 2H), 3.22 (s, 3H), 3.07 (br d, 6H), 2.31 (s, 3H), 2.08 (s, 3H), 1.64 (t, J = 7.3 Hz, 4H) |
| 7.002 | nPr | Me | SO₂Me | 1H NMR(400 MHz,d4-methanol)7.89(d,1H),7.38-7.30(m,2H), 5.49(s,1H), 4.34(t,2H), 3.23(s,3H), 3.08(brd,6H), 2.28(s,3H), 2.08-1.93(m,2H), 0.98(t,3H) |
| 7.003 | —CH₂CH₂OCH₃ | Me | SO₂Me | 9.74-9.22(m,1H), 7.94(d,1H), 7.26-7.23 (m, 2H), 4.62(t,2H), 3.84(t,2H), 3.37(s,3H), 3.22(s,3H), 3.07(d,6H), 2.33(s,3H) |

BIOLOGICAL EXAMPLES

Seeds of a variety of test species are sown in standard soil in pots (*Lolium perenne* (LOLPE), *Amaranthus retoflexus* (AMARE), *Abutilon theophrasti* (ABUTH), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 500 g/h unless otherwise indicated. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

TABLE B1

| | POST Application | | | | | PRE Application | | | | |
|---|---|---|---|---|---|---|---|---|---|---|
| Compound | AMARE | ABUTH | SETFA | ECHCG | IPOHE | AMARE | ABUTH | SETFA | ECHCG | IPOHE |
| 1.017 | 5 | 5 | 5 | 5 | 5 | 5 | 5 | 5 | 5 | 5 |
| 1.025 | 5 | 5 | 5 | 5 | 5 | 5 | 5 | 5 | 5 | 5 |
| 1.027 | 5 | 5 | 5 | 5 | 5 | 5 | 5 | 5 | 5 | 5 |
| 1.031 | 5 | 5 | 5 | 5 | 5 | 5 | 5 | 5 | 5 | 4 |
| 1.041 | 5 | 5 | 5 | 5 | 5 | 5 | 5 | — | 5 | 5 |
| 1.049 | 5 | 5 | 5 | 5 | 5 | 5 | 5 | 5 | 5 | 5 |
| 1.055 | 5 | 5 | 5 | 5 | 5 | 5 | 5 | 5 | 5 | 5 |
| 1.057** | 5 | 5 | 5 | 5 | 5 | 5 | 5 | 5 | 5 | 5 |
| 1.129 | 5 | 5 | 5 | 5 | 5 | 5 | 5 | 5 | 5 | 5 |
| 1.130 | 5 | 5 | 5 | 5 | 5 | 5 | 5 | 5 | 5 | 5 |
| 1.131 | 5 | 5 | 5 | 5 | 5 | 5 | 5 | 5 | 5 | 5 |
| 1.132 | 5 | 5 | 5 | 5 | 5 | 5 | 5 | 5 | 5 | 5 |
| 1.135* | 5 | 5 | 5 | 3 | 5 | 5 | 5 | 5 | 5 | 5 |
| 1.139 | 5 | 5 | 5 | 5 | 4 | 5 | 5 | 5 | 5 | 5 |
| 1.140 | 5 | 5 | 5 | 5 | 5 | 5 | 5 | 5 | 5 | 5 |
| 1.142* | 5 | 5 | 5 | 5 | 5 | 5 | 5 | 5 | 5 | 4 |
| 1.144 | 5 | 5 | 5 | 5 | 5 | 5 | 5 | 5 | 5 | 5 |
| 1.145 | 4 | 3 | 5 | 5 | 4 | 5 | 5 | 5 | 5 | 4 |
| 1.148 | 5 | 4 | 5 | 5 | 4 | 5 | 5 | 5 | 5 | 5 |
| 2.017 | 5 | 4 | 5 | 5 | 4 | 5 | 5 | 4 | 5 | 5 |
| 2.025 | 5 | 5 | 5 | 5 | 5 | 5 | 5 | 5 | 5 | 3 |
| 2.027 | 5 | 5 | 5 | 5 | 5 | 5 | 5 | 5 | 5 | 4 |
| 2.031 | 5 | 5 | 5 | 5 | 4 | 5 | 4 | 5 | 5 | 4 |
| 2.049 | 5 | 5 | 5 | 5 | 5 | 5 | 5 | 5 | 5 | 5 |
| 2.055 | 5 | 4 | 5 | 5 | 4 | 5 | 5 | 5 | 5 | 5 |
| 2.129 | 5 | 5 | 5 | 5 | 5 | 5 | 5 | 3 | 3 | 2 |
| 2.131 | 5 | 4 | 5 | 5 | 3 | 5 | 3 | 5 | 5 | 2 |
| 2.132 | 5 | 5 | 5 | 5 | 5 | 5 | 5 | 5 | 5 | 5 |
| 2.140 | 5 | 5 | 5 | 5 | 4 | 5 | 5 | 5 | 5 | 4 |
| 2.142* | 5 | 5 | 5 | 5 | 5 | 5 | 3 | 5 | 5 | 1 |
| 2.143 | 5 | 5 | 5 | 5 | 5 | 5 | 5 | 5 | 5 | 5 |
| 2.144 | 5 | 5 | 5 | 5 | 4 | 5 | 5 | 5 | 5 | 3 |
| 2.148 | 5 | 5 | 5 | 5 | 3 | 5 | 5 | 5 | 5 | 5 |
| 3.017 | 3 | 5 | 5 | 5 | 5 | 5 | 5 | 4 | 5 | 5 |
| 3.025 | 5 | 5 | 5 | 5 | 5 | 5 | 5 | 4 | 5 | 4 |
| 3.049 | 5 | 5 | 5 | 5 | 5 | 5 | 5 | 5 | 5 | 5 |
| 3.057 | 5 | 5 | 5 | 5 | 5 | 5 | 5 | 5 | 5 | 5 |
| 3.130 | 5 | 5 | 5 | 5 | 4 | 5 | 5 | 5 | 5 | 5 |
| 4.014 | 5 | 5 | 5 | 5 | 5 | 5 | 5 | 5 | 5 | 5 |
| 4.016 | 4 | 3 | 5 | 5 | 4 | 5 | 5 | 5 | 5 | 5 |
| 5.016 | 4 | 3 | 5 | 5 | 4 | 5 | 5 | 5 | 5 | 5 |
| 7.002 | 5 | 5 | 5 | 5 | 4 | 5 | 5 | 5 | 5 | 5 |
| 7.003 | 5 | 5 | 5 | 5 | 5 | 5 | 5 | 5 | 5 | 5 |

— = No Data.

*Applied at 250 g/ha.

**Applied at 125 g/ha.

TABLE B2

A comparative experiment is conducted to show the advantage provided by the compounds of the present invention. Thus the biological performance of compound 1.049 of the present invention is compared with Compound C1, which is an aniline compound of the type referred to in WO2012/028579. Results are given as (%) phytotoxicity observed. The result demonstrates that compounds of the present invention provide much improved control of problematic weed species, exemplified using Echinochloa crus-galli (ECHCG) and Setaria faberi (SETFA), at similar application rates.

| Compound | Rate g/ha | POST Application | | PRE Application | |
|---|---|---|---|---|---|
| | | ECHCG | SETFA | ECHCG | SETFA |
| 1.049 | 31 | 90 | 90 | 90 | 90 |
| C1 | 31 | 0 | 20 | 0 | 0 |

The invention claimed is:

1. A compound of Formula (I):

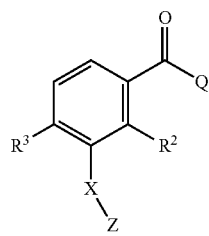

(I)

or an agronomically acceptable salt thereof, wherein:

$R^2$ is selected from the group consisting of halogen, $C_1$-$C_6$ alkyl, $C_3$-$C_6$-cycloalkyl, $C_1$-$C_6$ haloalkyl and —S(O)$_p$$C_1$-$C_6$ alkyl;

$R^3$ is selected from the group consisting of halogen, $C_1$-$C_6$ alkyl, $C_1$-$C_6$ haloalkyl and -S(O)$_p$$C_1$-$C_6$ alkyl;

Q is selected from the group consisting of $Q^1$, $Q^2$ and $Q^3$;

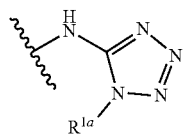

$Q^1$

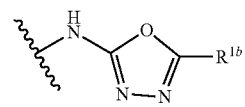

$Q^2$

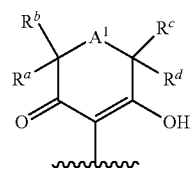

$Q^3$ $R^{1a}$ is $C_1$-$C_4$alkyl- or $C_1$-$C_3$-alkoxy-$C_1$-$C_3$-alkyl-;

$R^{1b}$ is selected from the group consisting of hydrogen, $C_1$-$C_4$alkyl- and $C_1$-$C_3$-alkoxy-$C_1$-$C_3$-alkyl-;

$A^1$ is selected from the group consisting of O, C(O) and $(CR^eR^f)$;

$R^a$, $R^b$, $R^c$, $R^d$, $R^e$ and $R^f$ are each independently selected from the group consisting of hydrogen and $C_1$-$C_4$alkyl wherein $R^a$ and $R^c$ may together form a $C_1$-$C_3$alkylene chain.

X is —$(CH_2)_n$- or —$(CH_2)_n$- O—$(CH_2)_n$-;

n is independently selected from 0, 1 and 2;

Z is $Z^1$ or $Z^2$

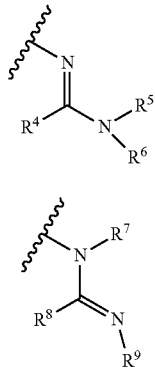

$R^4$ is selected from the group consisting of hydrogen, $C_1$-$C_6$ alkyl, $C_1$-$C_6$ haloalkyl and $C_3$-$C_6$ cycloalkyl;

$R^5$ is selected from the group consisting of hydrogen, $C_1$-$C_6$ alkyl and $C_1$-$C_6$ haloalkyl;

$R^6$ is selected from the group consisting of hydrogen, $C_1$-$C_6$ alkyl, $C_1$-$C_6$ haloalkyl, cyano and phenyl wherein the phenyl is optionally substituted by 1, 2 or 3 substituents selected from the group consisting of halogen, $C_1$-$C_6$ alkyl, $C_1$-$C_6$ haloalkyl and $C_1$-$C_6$ alkoxy; or $R^5$ and $R^6$ together are —$CH_2CH_2CH_2CH_2$, —$CH_2CH_2CH_2CH_2CH_2$- or —$CH_2CH_2OCH_2CH_2$-; and $R^7$ is selected from the group consisting of hydrogen and $C_1$-$C_6$ alkyl;

$R^8$ is selected from the group consisting of hydrogen, $C_1$-$C_6$ alkyl, $C_1$-$C_6$-haloalkyl and $C_3$-$C_6$-cycloalkyl;

$R^9$ is selected from the group consisting of hydrogen, cyano, $C_1$-$C_6$ alkyl and $C_1$-$C_6$alkoxy-; and p=0, 1 or 2.

2. The compound according to claim 1, wherein $R^2$ is selected from the group consisting of methyl, Cl, —$CF_3$ and —$SO_2$methyl.

3. The compound according to claim 1, wherein $R^3$ is selected from the group consisting of methyl, Cl, —$CF_3$ and —$SO_2$methyl.

4. The compound according to claim 1, wherein $R^1$ is selected from the group consisting of methyl, ethyl and n-propyl.

5. The compound according to claim 1, wherein Q is $Q^1$ and Z is $Z^1$.

6. The compound according to claim 5, wherein X is —$(CH_2)_n$- and n is 0.

7. The compound according to claim 1, wherein Q is $Q^2$ and Z is $Z^1$.

8. The compound according to claim 7, wherein X is —$CH_2O$—.

9. The compound according to claim 1, wherein Q is $Q^3$ and Z is $Z^1$.

10. The compound according to claim 1, wherein Q is $Q^1$ and Z is $Z^2$.

11. A herbicidal composition comprising a compound according to claim 1 and an agriculturally acceptable formulation adjuvant.

12. A herbicidal composition according to claim 11, further comprising at least one additional pesticide.

13. A herbicidal composition according to claim 12, wherein the additional pesticide is a herbicide or herbicide safener.

14. A method of controlling weeds at a locus comprising applying to the locus of a weed controlling amount of a composition according to claim 1.

* * * * *